United States Patent
Ragosta et al.

(10) Patent No.: US 11,896,338 B2
(45) Date of Patent: Feb. 13, 2024

(54) MANUAL RELEASE FOR MEDICAL DEVICE DRIVE SYSTEM

(71) Applicant: Intuitive Surgical Operations, Inc., Sunnyvale, CA (US)

(72) Inventors: Nicholas H. Ragosta, San Francisco, CA (US); Matthew A. Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/987,481

(22) Filed: Nov. 15, 2022

(65) Prior Publication Data

US 2023/0114904 A1    Apr. 13, 2023

Related U.S. Application Data

(63) Continuation of application No. 17/374,681, filed on Jul. 13, 2021, now Pat. No. 11,529,206, which is a
(Continued)

(51) Int. Cl.
*A61B 34/00*    (2016.01)
*A61B 1/00*    (2006.01)
(Continued)

(52) U.S. Cl.
CPC .......... *A61B 34/71* (2016.02); *A61B 1/00133* (2013.01); *F16H 55/17* (2013.01);
(Continued)

(58) Field of Classification Search
CPC ..... A61B 34/71; A61B 1/00133; F16H 55/17; F16H 59/02
(Continued)

(56) References Cited

U.S. PATENT DOCUMENTS

| 2,091,317 A | 8/1937 | Hill |
| 2,906,143 A | 9/1959 | Musser |

(Continued)

FOREIGN PATENT DOCUMENTS

| AU | 2014208189 A1 * | 4/2015 | ........... A61B 17/068 |
| CN | 1939228 A | 4/2007 | |

(Continued)

OTHER PUBLICATIONS

Litvin F.L., et al., "Face Gear Drive with Helical Involute Pinion: Geometry, Generation by a Shaper and a Worm, Avoidance of Singularities and Stress Analysis," NASA/CR-2005-213443, ARL-CR-557, Feb. 2005, 62 pages.

(Continued)

*Primary Examiner* — Hoan H Tran

(57) ABSTRACT

A medical device drive system can include a rotational input, a coupling member engaged with the rotational input, a first gear having an engagement feature sized and shaped to engage with the coupling member, and a second gear coupled with the first gear, the second gear coupled to a movable element. The system can have a first system state and a second system state. In the first system state the coupling member is not engaged with the engagement feature and the first gear rotates without moving the coupling member. In the second system state the coupling member is engaged with the engagement feature of the first gear and rotation of the rotational input turns the coupling member, the first gear, and the second gear to move the movable element.

20 Claims, 22 Drawing Sheets

Related U.S. Application Data continuation of application No. 15/927,926, filed on Mar. 21, 2018, now Pat. No. 11,076,926.

(60) Provisional application No. 62/474,360, filed on Mar. 21, 2017.

(51) Int. Cl.
*F16H 55/17* (2006.01)
*F16H 59/02* (2006.01)
*A61B 17/00* (2006.01)
*F16H 63/30* (2006.01)
*A61B 34/30* (2016.01)

(52) U.S. Cl.
CPC ........ *F16H 59/02* (2013.01); *A61B 17/00234* (2013.01); *A61B 2017/00477* (2013.01); *A61B 2034/301* (2016.02); *F16H 2059/0221* (2013.01); *F16H 2059/0295* (2013.01); *F16H 2063/3076* (2013.01); *F16H 2712/00* (2013.01)

(58) Field of Classification Search
USPC .......................................................... 606/130
See application file for complete search history.

(56) References Cited

U.S. PATENT DOCUMENTS

| | | | |
|---|---|---|---|
| 3,312,496 A | 4/1967 | Albert et al. |
| 4,139,104 A | 2/1979 | Mink |
| 5,099,705 A | 3/1992 | Dravnieks |
| 5,792,135 A | 8/1998 | Madhani et al. |
| 5,807,377 A | 9/1998 | Madhani et al. |
| 5,855,583 A | 1/1999 | Wang et al. |
| 5,876,325 A | 3/1999 | Mizuno et al. |
| 6,007,550 A | 12/1999 | Wang et al. |
| 6,318,199 B1 | 11/2001 | Buck |
| 6,817,974 B2 | 11/2004 | Cooper et al. |
| 6,994,708 B2 | 2/2006 | Manzo |
| 7,083,571 B2 | 8/2006 | Wang et al. |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,666,191 B2 | 2/2010 | Orban, III et al. |
| 7,935,130 B2 | 5/2011 | Williams |
| 7,963,913 B2 | 6/2011 | Devengenzo et al. |
| 8,142,447 B2 | 3/2012 | Cooper et al. |
| 8,224,484 B2 | 7/2012 | Swarup et al. |
| 8,241,271 B2 | 8/2012 | Millman et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,602,031 B2 | 12/2013 | Reis et al. |
| 8,771,270 B2 | 7/2014 | Burbank |
| 8,800,838 B2 | 8/2014 | Shelton, IV |
| 8,992,565 B2 | 3/2015 | Brisson et al. |
| 9,028,494 B2 | 5/2015 | Shelton, IV et al. |
| 9,078,684 B2 | 7/2015 | Williams |
| 9,121,494 B2 | 9/2015 | Buchleitner et al. |
| 9,204,923 B2 | 12/2015 | Manzo et al. |
| 9,232,979 B2 | 1/2016 | Parihar et al. |
| 9,259,274 B2 | 2/2016 | Prisco |
| 9,524,022 B2 | 12/2016 | Nakayama |
| 9,572,616 B2 | 2/2017 | Vaughn |
| 9,737,373 B2 | 8/2017 | Schuh |
| 9,750,578 B2 | 9/2017 | Alden et al. |
| 9,839,439 B2 | 12/2017 | Cooper et al. |
| 9,913,694 B2 | 3/2018 | Brisson |
| 9,931,106 B2 | 4/2018 | Au et al. |
| 9,993,313 B2 | 6/2018 | Schuh et al. |
| 10,076,348 B2 | 9/2018 | Anderson et al. |
| 10,201,365 B2 | 2/2019 | Boudreaux |
| 10,288,837 B2 | 5/2019 | Miyatani et al. |
| 10,314,583 B2 | 6/2019 | Smith et al. |
| 10,357,321 B2 | 7/2019 | Donlon et al. |
| 10,470,830 B2 | 11/2019 | Hill et al. |
| 10,478,256 B2 | 11/2019 | Shelton, IV et al. |
| 10,543,051 B2 | 1/2020 | Schena et al. |
| 10,624,709 B2 | 4/2020 | Remm |
| 10,772,690 B2 | 9/2020 | Prisco |
| 10,779,898 B2 | 9/2020 | Hill et al. |
| 10,806,530 B2 | 10/2020 | Liao et al. |
| 10,881,280 B2 | 1/2021 | Baez, Jr. |
| 10,932,868 B2 | 3/2021 | Solomon et al. |
| 11,020,112 B2 | 6/2021 | Shelton, IV et al. |
| 11,045,270 B2 | 6/2021 | Shelton, IV et al. |
| 11,076,926 B2 | 8/2021 | Ragosta et al. |
| 11,118,661 B2 | 9/2021 | Abbott |
| 2002/0111635 A1 | 8/2002 | Jensen et al. |
| 2005/0119527 A1 | 6/2005 | Banik et al. |
| 2006/0190034 A1 | 8/2006 | Nishizawa et al. |
| 2007/0043338 A1 | 2/2007 | Moll et al. |
| 2007/0137371 A1 | 6/2007 | Devengenzo et al. |
| 2007/0208375 A1 | 9/2007 | Nishizawa et al. |
| 2007/0232858 A1 | 10/2007 | Macnamara et al. |
| 2008/0009838 A1 | 1/2008 | Schena et al. |
| 2008/0046122 A1 | 2/2008 | Manzo et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2010/0011900 A1 | 1/2010 | Burbank et al. |
| 2010/0318101 A1 | 12/2010 | Choi et al. |
| 2011/0015650 A1 | 1/2011 | Choi et al. |
| 2011/0071543 A1 | 3/2011 | Prisco et al. |
| 2011/0118754 A1 | 5/2011 | Dachs, II et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0109186 A1 | 5/2012 | Parrott et al. |
| 2012/0123441 A1 | 5/2012 | Au et al. |
| 2012/0184955 A1 | 7/2012 | Pivotto et al. |
| 2012/0239060 A1 | 9/2012 | Orban, III et al. |
| 2012/0289974 A1 | 11/2012 | Rogers et al. |
| 2013/0046318 A1 | 2/2013 | Radgowski et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0100558 A1 | 4/2014 | Schmitz et al. |
| 2014/0257333 A1 | 9/2014 | Blumenkranz |
| 2014/0276723 A1 | 9/2014 | Parihar et al. |
| 2014/0309625 A1 | 10/2014 | Okamoto et al. |
| 2015/0005786 A1 | 1/2015 | Burbank |
| 2015/0051034 A1 | 2/2015 | Cooper et al. |
| 2015/0150636 A1 | 6/2015 | Hagn et al. |
| 2015/0157355 A1 | 6/2015 | Price et al. |
| 2016/0058443 A1 | 3/2016 | Yates et al. |
| 2016/0151115 A1 | 6/2016 | Karguth et al. |
| 2016/0166342 A1 | 6/2016 | Prisco et al. |
| 2016/0296219 A1 | 10/2016 | Srivastava et al. |
| 2016/0361049 A1 | 12/2016 | Dachs, II et al. |
| 2017/0022754 A1 | 1/2017 | Nien et al. |
| 2017/0165017 A1 | 6/2017 | Chaplin et al. |
| 2017/0172672 A1 | 6/2017 | Bailey et al. |
| 2018/0055583 A1 | 3/2018 | Schuh et al. |
| 2018/0080533 A1 | 3/2018 | Awtar |
| 2018/0229021 A1 | 8/2018 | Donlon et al. |
| 2019/0038282 A1 | 2/2019 | Shelton, IV et al. |
| 2019/0099227 A1 | 4/2019 | Rockrohr |
| 2019/0117325 A1 | 4/2019 | Kishi |
| 2019/0125468 A1 | 5/2019 | Adams |
| 2019/0159846 A1 | 5/2019 | Yates et al. |
| 2019/0201022 A1 | 7/2019 | Schoettgen et al. |
| 2019/0223960 A1 | 7/2019 | Chaplin et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0298323 A1 | 10/2019 | Lambrecht et al. |
| 2019/0328467 A1 | 10/2019 | Waterbury et al. |

(56) References Cited

U.S. PATENT DOCUMENTS

| | | |
|---|---|---|
| 2020/0093554 A1 | 3/2020 | Schuh et al. |
| 2021/0169591 A1 | 6/2021 | Kapadia |
| 2021/0196408 A1 | 7/2021 | Hoffman et al. |
| 2021/0196413 A1 | 7/2021 | Inoue |
| 2021/0372508 A1 | 12/2021 | Abbott |
| 2022/0000572 A1 | 1/2022 | Ragosta et al. |
| 2022/0015847 A1 | 1/2022 | Kadokura |
| 2022/0039895 A1 | 2/2022 | Adams et al. |
| 2022/0096067 A1 | 3/2022 | Beckman et al. |
| 2022/0096082 A1 | 3/2022 | Beckman et al. |
| 2022/0128133 A1 | 4/2022 | Cooper et al. |
| 2022/0249182 A1 | 8/2022 | Definis et al. |

FOREIGN PATENT DOCUMENTS

| | | | | |
|---|---|---|---|---|
| CN | 101893060 A | | 11/2010 | |
| CN | 104582628 | * | 4/2015 | |
| CN | 109505951 A | | 3/2019 | |
| FR | 3014678 A1 | * | 6/2015 | ......... A61B 18/1477 |
| JP | H06114000 A | | 4/1994 | |
| JP | H10249777 A | | 9/1998 | |
| JP | 2005288590 A | | 10/2005 | |
| WO | WO-9729690 A1 | | 8/1997 | |
| WO | WO-2009039506 A1 | | 3/2009 | |
| WO | WO-2012068156 A2 | | 5/2012 | |
| WO | WO-20160736137 A1 | | 5/2016 | |
| WO | WO-2016172299 A1 | | 10/2016 | |
| WO | WO-2016189284 A1 | | 12/2016 | |
| WO | WO-2017188851 A1 | | 11/2017 | |
| WO | WO-2018013313 A1 | | 1/2018 | |
| WO | WO-2018094191 A1 | | 5/2018 | |
| WO | WO-2021155707 A1 | | 8/2021 | |
| WO | WO-2023055684 A2 | | 4/2023 | |

OTHER PUBLICATIONS

Litvin F.L., et al., "Handbook on Face Gear Drives with a Spur Involute Pinion," NASA/CR-2000-209909, ARL-CR-447, Mar. 2000, 106 pages.

Smith L.J., "The Involute Helicoid and the Universal Gear," Gear Technology. Nov./Dec. 1990, pp. 18-27.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

MANUAL RELEASE FOR MEDICAL DEVICE DRIVE SYSTEM

CLAIM OF PRIORITY

This application is a continuation of and claims the benefit of priority under 35 U.S.C. § 120 to U.S. patent application Ser. No. 17/374,681, filed on Jul. 13, 2021, which is a continuation of and claims the benefit of priority under 35 U.S.C. § 120 to U.S. patent application Ser. No. 15/927,926, filed on Mar. 21, 2018, which claims the benefit of priority under 35 U.S.C. § 119(e) to U.S. Provisional Patent Application Ser. No. 62/474,360, filed on Mar. 21, 2017, each of which is incorporated by reference herein in its entirety.

BACKGROUND

Medical device systems can include components that are driven by drive mechanisms such as electric motors. Drive components such as gears, levers, and tubes can be used to translate movement through a drive system to a medical tool. For example, surgical systems can include tools that are controlled and driven by mechanical drive systems. Surgical systems can include tools such as cutters, staplers, and cautery tools. These types of tools can be used, for example, in minimally invasive surgical procedures.

In some procedures, an endoscope is inserted into the patient's body to provide a view of internal organs or other features inside a patient. A procedure that involves introduction of an endoscope is called an endoscopy. A common form of endoscopy, called laparoscopy, involves insertion of an endoscope through the abdominal wall of a patient. Endoscopic and laparoscopic procedures can involve drive systems that control surgical instruments inside the patient.

SUMMARY

This document discusses, among other things, systems and methods to manually operate a medical device drive system. It can be useful to manually operate a medical device drive system when a surgical element such as an instrument cannot be retracted using a telerobotic system due to a power failure or some other event during a surgical procedure.

An example (e.g., "Example 1") of subject matter (e.g., a system) may include a rotational input, a coupling member engaged with the rotational input, a first gear having an engagement feature sized and shaped to engage with the coupling member, and a second gear coupled with the first gear, the second gear coupled to a movable element. An example system may have a first system state and a second system state, where in the first system state the coupling member is not engaged with the engagement feature and the first gear rotates without moving the coupling member, and in the second system state the coupling member is engaged with the engagement feature of the first gear and rotation of the rotational input turns the coupling member, the first gear, and the second gear to move the movable element.

In Example 2, the medical device drive system of Example 1 may optionally be configured such that the coupling member is slidably coupled to the rotational input, and the coupling member slides away from the rotational input as the rotational input is turned in a first direction.

In Example 3, the medical device drive system of Example 1 or 2 may optionally be configured such that the first gear includes a protrusion including a first set of teeth and the coupling member includes a second set of teeth. The first set of teeth may be sized and shaped to engage the second set of teeth when the coupling member is advanced toward the first gear.

In Example 4, the medical device drive system of Example 3 may optionally be configured such that the first set of teeth and the second set of teeth are arranged around a rotational axis. The coupling member may be slidable along the rotational axis and the coupling member and the first gear being rotatable around the rotational axis.

In Example 5, the medical device drive system of any one or any combination of Examples 1~4 may further include a rotational resistance member that resists rotation of the coupling member. In an example, the rotational resistance member may be the ratchet. In another example, the rotational resistance member may include a belt, and a belt coupling (e.g., pulley) may be configured to translate distally as the coupling member moves distally.

In Example 6, the medical device drive system of Example 5 may optionally be configured such that in the first system state, a first moment exerted by the rotational resistance member on the coupling member exceeds a second moment exerted by the rotational input on the coupling member such that turning the rotational input biases the coupling member away from the rotational input, and in the second system state the first moment exerted by the a rotational resistance member on the coupling member is less than the first exerted by the rotational input on the coupling member such that turning the rotational input in the second state rotates the coupling member. In an example, when a force is applied to the coupling member, the coupling member initially moves distally through an axial range of motion, and then when the coupling member reaches a most distal position, the coupling member rotates when a force on the input member creates a moment that is large enough to overcome a counter-moment from a force exerted by the rotational resistance member.

In Example 7, the medical device drive system of Example 6 may optionally be configured such that the coupling member includes a ramp and the rotational input is sized and shaped to engage the ramp, wherein rotation of the rotational input engages the rotational input against the ramp and biases the coupling member away from the rotational input and toward the first gear. The rotational input may, for example, include a ramp that is sized and shaped to engage with the ramp on the coupling member. The ramps may, for example, follow a circumferential path around a common axis. In an example configuration, the coupling input may include two or more ramps, and the rotational input may be sized and shaped to engage both ramps.

In Example 8, the medical device drive system of claim 6 may optionally be configured such that the rotational input includes a ramp and the coupling member is sized and shaped to engage the ramp, wherein rotation of the rotational input engages the ramp against the coupling member and biases the coupling member away from the rotational input and toward the first gear.

In Example 9, the medical device drive system of any one or any combination of Examples 1-8 may further include a third gear engaged with the first gear and the second gear, the first gear coupled to the third gear with the second gear.

In Example 10, the medical device drive system of any one or any combination of Examples 1-9 may further include a spring between the coupling member and the first gear, the spring sized and shaped to bias the coupling member away from the first gear. The system may optionally be configured such that in a neutral position the coupling member is disengaged from the first gear.

In Example 11, the medical device drive system of any one or any combination of Examples 1-10 may further include a manual drive lock sized and shaped to engage the coupling member, wherein the manual drive lock prevents the coupling member from disengaging from the first gear.

In Example 12, the medical device drive system of Example 11 may optionally be configured such that the medical device drive interfaces with an adaptor to operatively couple the drive system to a computerized control system. The adaptor may include a switch engagement portion, such as a latch, that is configured to engage a switch to activate the manual drive lock, such that in a first adaptor state the medical device drive system is not interfaced with the adaptor and the and the manual drive lock is not engaged with the coupling member, and in a second adaptor state the medical device drive system is engaged with the adaptor and the manual drive lock is biased toward an locking feature on the coupling member. In an example, when coupling member engages the first gear, the manual drive lock engages the locking feature on the coupling member and locks the coupling member into engagement with the first gear.

An Example medical device drive system ("Example 13") may include a first gear, a second gear coupled to a drive train that is configured to retract an instrument, the second gear coupled to the first gear, and a manual input that is selectively engageable with the first gear. The system may optionally be configured such that in a first state the manual input is not engaged with the first gear, and actuation of the manual input does not turn the first gear and does not retract the instrument, and in a second state the manual input is engaged with the first gear, and actuation of the manual input turns the first gear and the second gear to retract the instrument.

In Example 14, the medical device drive system of Example 13 may further include a coupling member, and may optionally be configured such that the manual input is selectively engageable with the first gear with by the coupling member.

In Example 15, the medical device drive system of Example 14 may optionally be configured such that in the first state actuation of the manual input advances the coupling member toward the first gear until the coupling member engages the first gear.

In Example 16, the medical device drive system of Example 15 may further include a manual drive lock, wherein when the manual drive lock is activated the system is locked in the second state by manual drive lock when the system is advanced from the first state to the second state.

In Example 17, the medical device drive system of Example 15 or 16 may optionally be configured such that the manual input is biased toward the first state by a spring.

In Example 18, the medical device drive system of any one or any combination of Examples 13-17 may further include a third gear coupled to the first gear and the second gear, the third gear being selectively engageable with a telerobotic control system.

An example medical device drive system ("Example 19") may include a means for driving a manual input against a coupling member, a means for engaging the coupling member with a first gear; and a means for retracting an instrument. The means for retracting the instrument may be coupled to the first gear. The system may be configured such that in a first state the coupling member is not engaged with the first gear and actuating the manual input moves the coupling member toward the first gear but does not drive the first gear, and in a second state the coupling member is engaged with the first gear and actuating the manual input drives the first gear and retracts the instrument.

In Example 20, the medical device drive system of Example 19 may further include a means for locking the coupling member with the first gear.

In Example 21, the medical device drive system of Example 19 or 20 may optionally be configured such that the means for engaging the coupling member with the first gear includes a means for advancing the coupling member toward the first gear, and the system may further include a means for resisting rotation of the coupling member as the coupling member advances toward the first gear. In an example, the means for resisting rotation of the coupling member as the coupling member advances toward the first gear may include a ratchet, or a belt on a sliding belt pulley, or a belt that slides distally with respect to a pulley or belt tensioning member, or a belt that slides with respect to the coupling member.

In Example 22, the medical device drive system of any one or any combination of Examples 19-21 may further include a telerobotic control system coupled to the means for retracting the instrument. In an example, the first state the telerobotic control system drives the means for retracting an instrument without engaging the first gear, and in the second state the manual input drives the first gear and the means for retracting the instrument.

An example method of controlling an instrument ("Example 23") may include driving a manual input against a coupling member to advance the coupling member into engagement with a first gear, driving the first gear with the coupling member and manual input, and driving a drive train with the first gear to retract a moveable element.

In Example 24, the method of Example 23 may further include locking the coupling member in an engaged position with a manual lock switch that engages the coupling member.

In Example 25, the method of Example 23 or 24 may further include driving the drive train with a telerobotic control system to retract the movable element when the coupling member is not engaged with the first gear.

In Example 26, the method of any one or any combination of Examples 23-25 may further include biasing the coupling member out of engagement with the first gear when the manual input is released.

An example (e.g., "Example 27") of subject matter (e.g., a system or apparatus) may optionally combine any portion or combination of any portion of any one or more of Examples 1-26 to include "means for" performing any portion of any one or more of the functions or methods of Examples 1-26, or a "machine-readable medium" (e.g., massed, non-transitory, etc.) including instructions that, when performed by a machine, cause the machine to perform any portion of any one or more of the functions or methods of Examples 1-26.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Medical device drive systems can be used to control an instrument that is coupled to a drive system with a shaft. A teleoperated surgical system, for example, can employ a medical device drive system to control a surgical instrument that can be inserted into a patient to perform a surgical procedure.

Manipulation of a surgical instrument during a teleoperated surgical procedure can be difficult, due to factors such as space constraints, the size of components, the need for precision and accuracy during surgery, and the presence of multiple tools in the body.

The present inventors have recognized, among other things, that a manual input system for a medical device drive train can be formed with a coupling member that can be engaged and disengaged with a drive train. A system can enable, for example, manual retraction of a device drive train in the event of a power outage, system fault, torque limit trigger, jam, or other event during a procedure. In some examples, manual retraction can be controlled with a manual input, such as a knob. The system can be configured so that the manual input (e.g., knob) does not turn when the drive system is being driven by the system. The system can also be configured so that a manual input can only retract the drive system, and not advance it. In some examples, the system can be configured so that the manual input cannot apply enough torque to the manual input to damage the drive train. The system can also be configured so that the manual input can apply high forces in the retraction direction to the drive train to enable retraction during a procedure.

An example medical device drive system can include a rotational input and a coupling member engaged with the rotational input. The rotational input can be a manual input. The system can also include a first gear having an engagement feature sized and shaped to engage with the coupling member, and a second gear coupled with the first gear. The second gear coupled to a movable element, such as a surgical instrument. The system may have a first system state, in which the coupling member is not engaged with the engagement feature and the first gear rotates without moving the coupling member. This may enable, for example, a drive train to be driven by a computer-controlled system, without rotation of the rotational input when the gears are driven. The system may also have a second system state, in which the coupling member is engaged with the engagement feature of the first gear and rotation of the rotational input turns the coupling member, the first gear, and the second gear to move the instrument. The system may include one or more additional gears between the first and second gear, or coupled to the first or second gear to enable connection to other aspects of the system, such as elements of a robot-assisted minimally invasive surgical system.

Figure 1A:
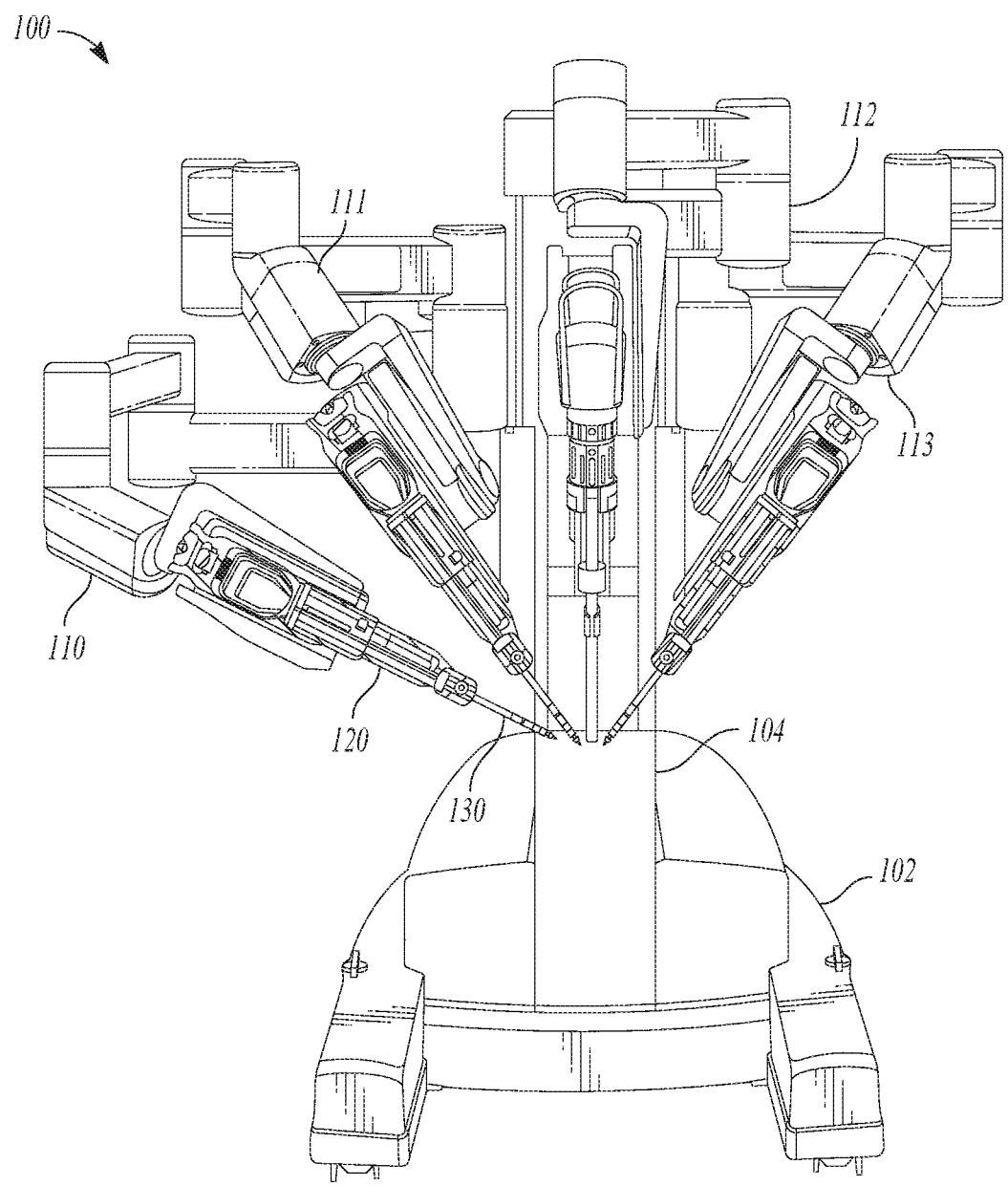
FIG. 1A is an illustration of an example instrument system for use in robot-assisted minimally invasive surgery.
Figure 1B:
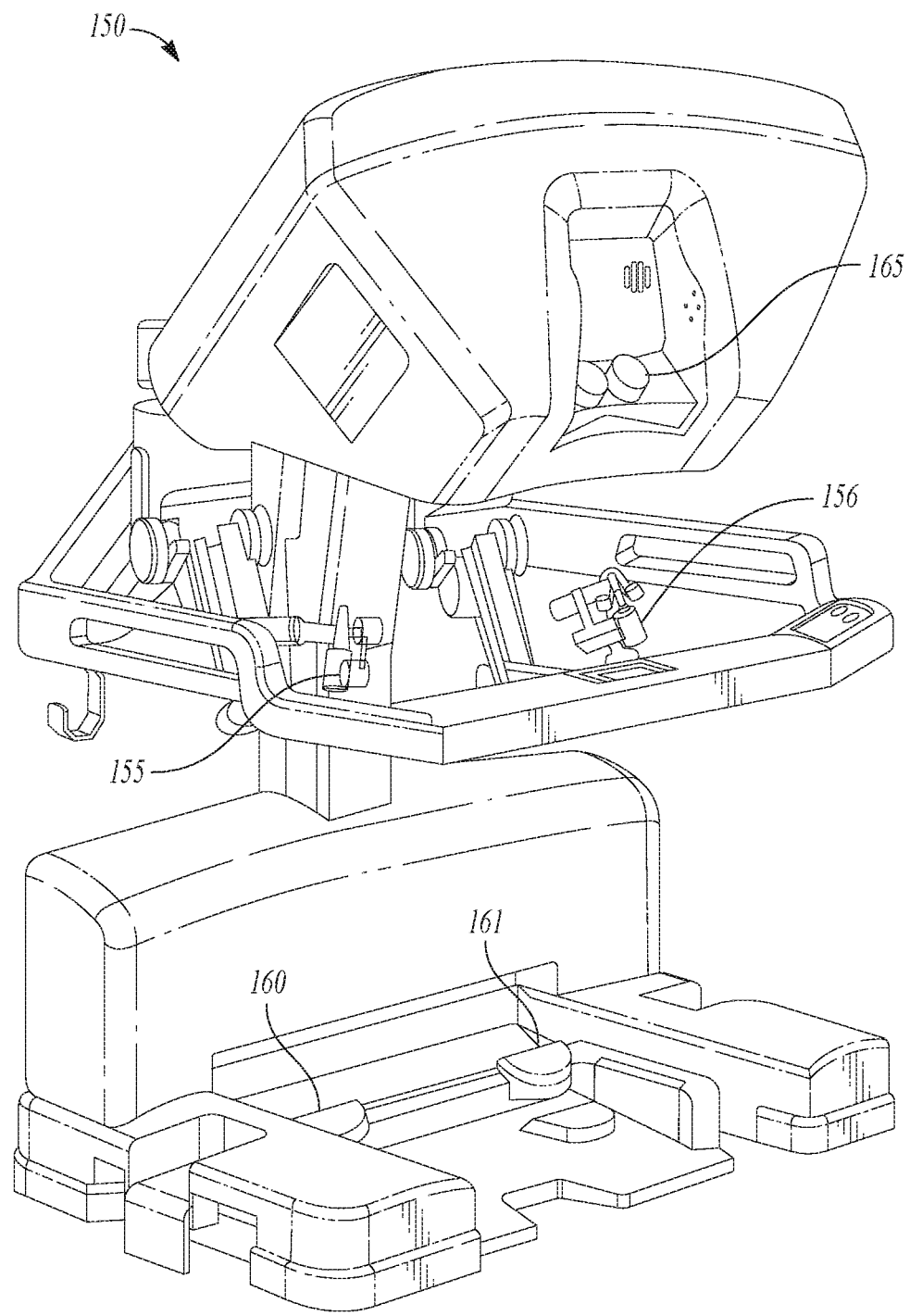
FIG. 1B is an illustration of an example physician console for use in robot-assisted minimally invasive surgery.
Figure 1C:
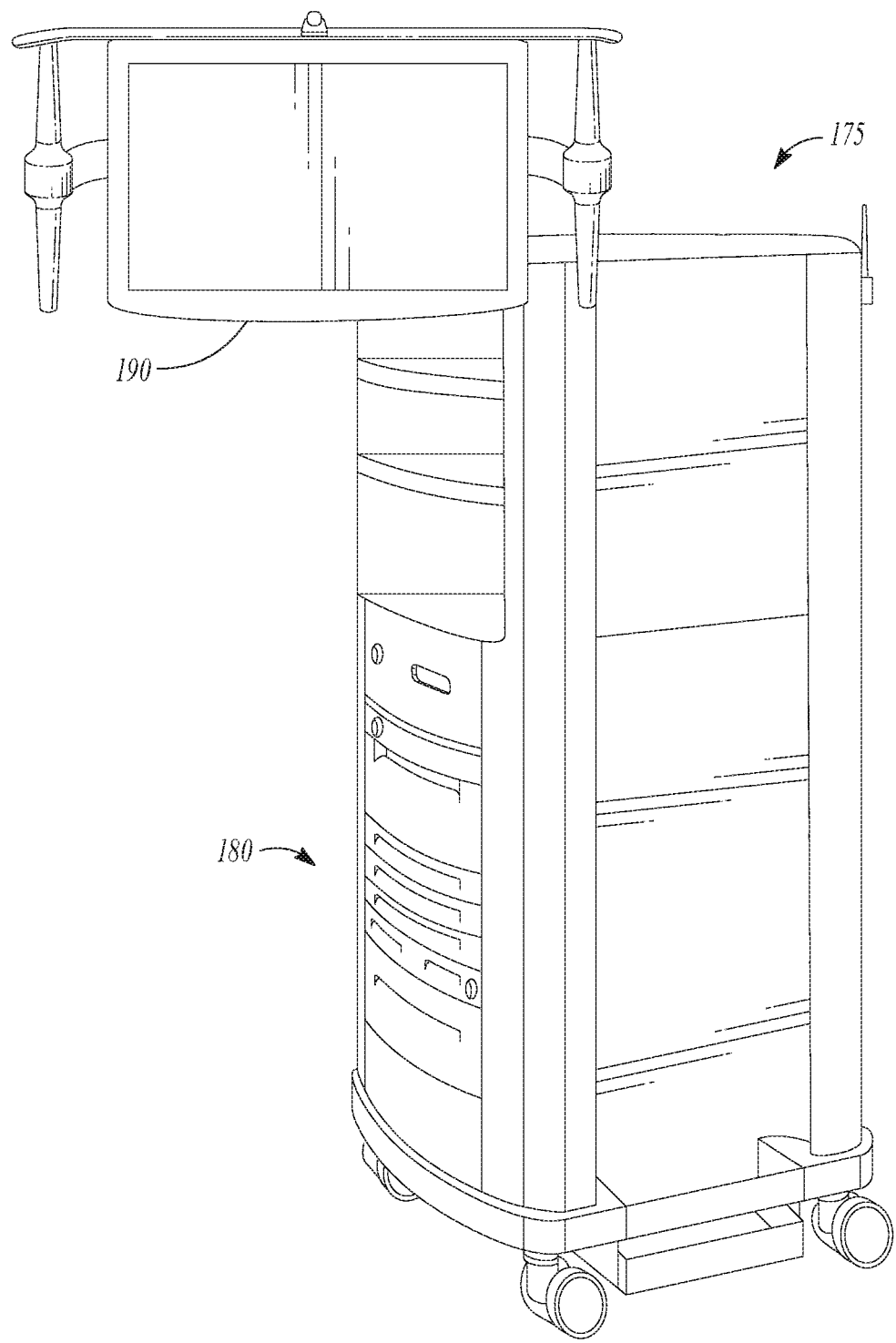
FIG. 1C is an illustration of an example control cart for use in robot-assisted minimally invasive surgery.

FIGS. 1A, 1B, and 1C illustrate an example robot-assisted minimally invasive surgical system. FIG. 1A shows an instrument system 100 (sometimes known as a "patient side cart") that can be situated near a patient operating table (not shown). FIG. 1B shows a surgeon console 150 that can include controls and a viewing system. FIG. 1C shows a control cart 175 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure.

Through movement of the manipulator arms, the orientation of the instrument can be controlled in multiple dimensions, e.g. lateral, horizontal, vertical, angular movements in one, two, or three planes.

FIG. 1B shows an example physician console 150. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 150 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 150 can be transmitted to the equipment 180 on the control cart, which can interpret the inputs and generate commands that are transmitted to the patient side cart 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 1D:
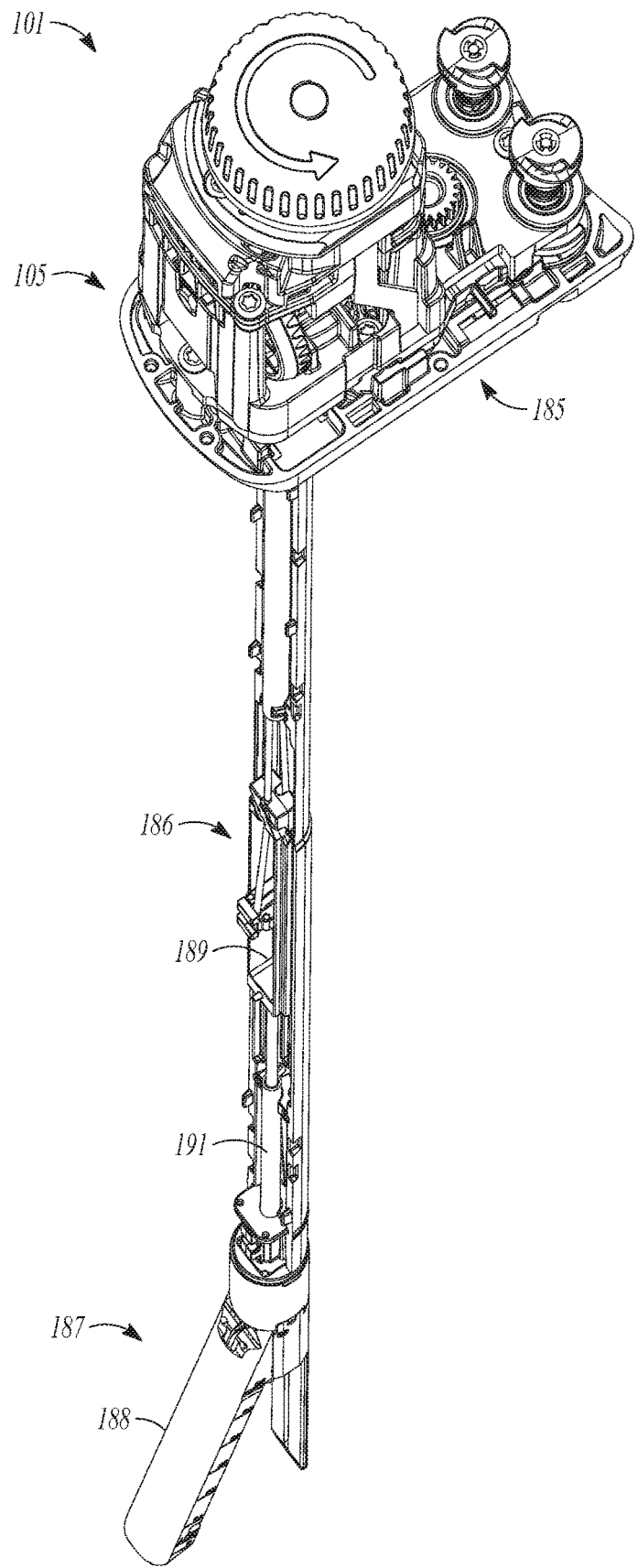
FIG. 1D is a perspective view of an example medical device drive system connected to an example medical tool.

FIG. 1D shows an example medical device system 101 that can be mounted on and used with the instrument system 100 shown in FIG. 1A. The medical device system 101 can include a proximal portion 105 including an interface 185 that can couple to a computerized control system such as the system illustrated in FIGS. 1A, 1B, and 1C, a middle portion 186 that can include drive components such as a drive member (not shown in FIG. 1D), and a distal portion 187 that can include a surgical tool 188. The middle portion 186 can include portions of a drive train 189 that can couple the proximal portion 105 to a moveable element 191 that can be coupled to the surgical tool 188. The surgical tool 188 can, for example, be any of a variety of surgical tools, such as a cutter, grasper, a cautery tool, a camera, a light, or a surgical stapler. The surgical tool 188 can be the instrument 130 shown in FIG. 1A. For the purpose of this document, the terms "tool" and "instrument" are interchangeable.

Figure 2:
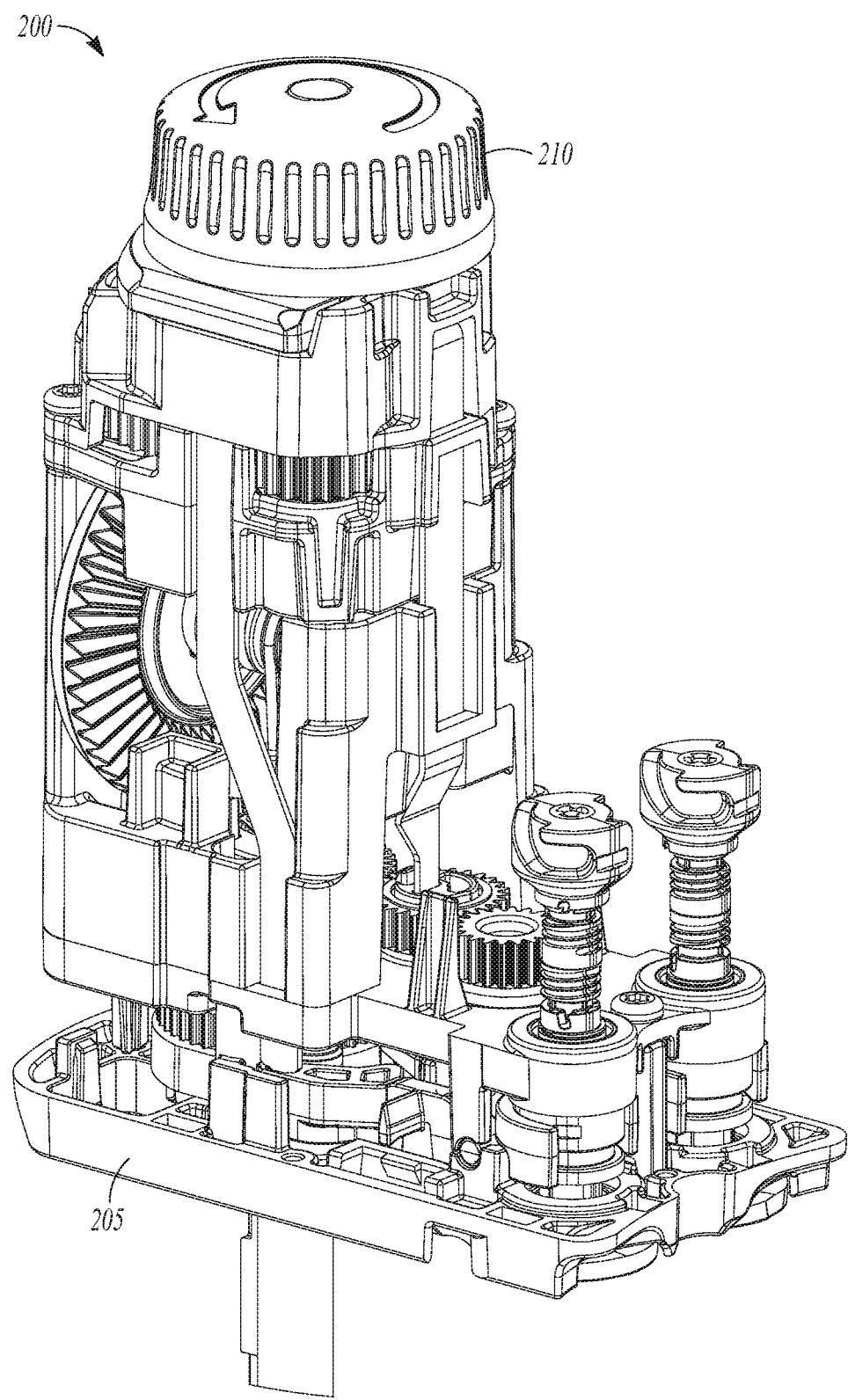
FIG. 2 is a perspective view of a proximal end of a drive system.

FIG. 2 is a perspective view of a proximal end of a drive system. The drive system 200 can be mounted on a chassis 205. The drive system 200 can include a manual input 210 that may be a rotational input such as a knob. The manual input 210 can engage other components (not shown in FIG. 2) to drive a moveable element and actuate an instrument or tool, such as a surgical stapler or cuter.

Figure 3A:
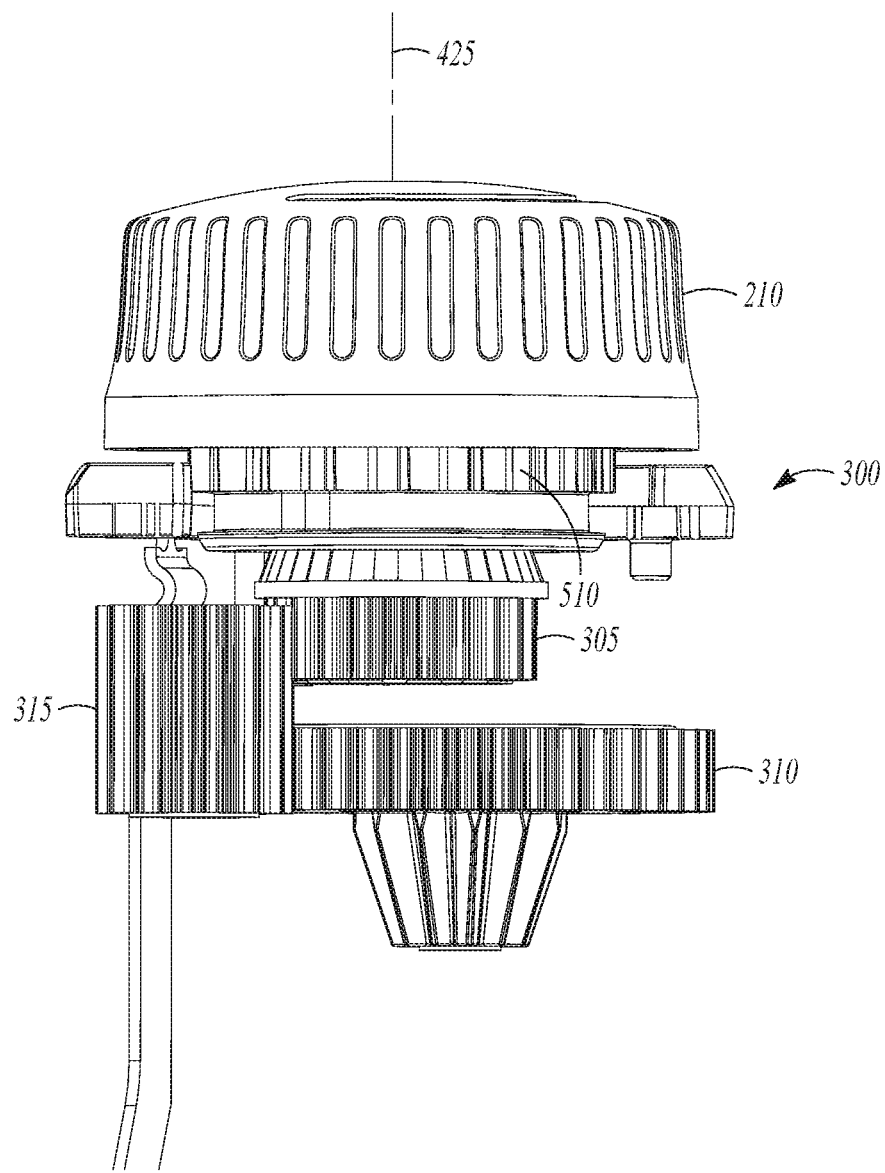
FIG. 3A is a side view of drive components in a proximal end of a drive system.
Figure 3B:
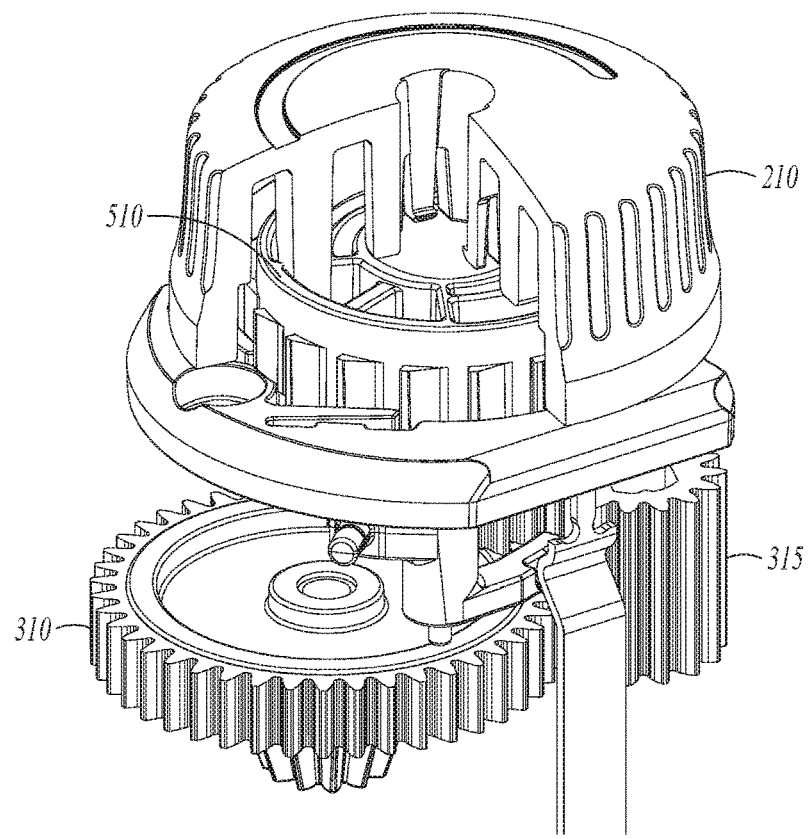
FIG. 3B is a perspective view of drive components in a proximal end of a drive system.

FIGS. 3A and 3B are a side and perspective views of drive components in a proximal end 300 of a drive system. The manual input 210 can be engaged with a coupling member 510 (better shown in subsequent figures) that can engage with a first gear 305 that can be coupled with a second gear 310 that can be engaged with a moveable component to move or actuate an instrument or tool. In some examples, the first gear 305 can be coupled to the second gear 310 with a third gear 315, which can optionally be coupled to computerized control system, which can be part of a robot-assisted surgical system.

Figure 4:
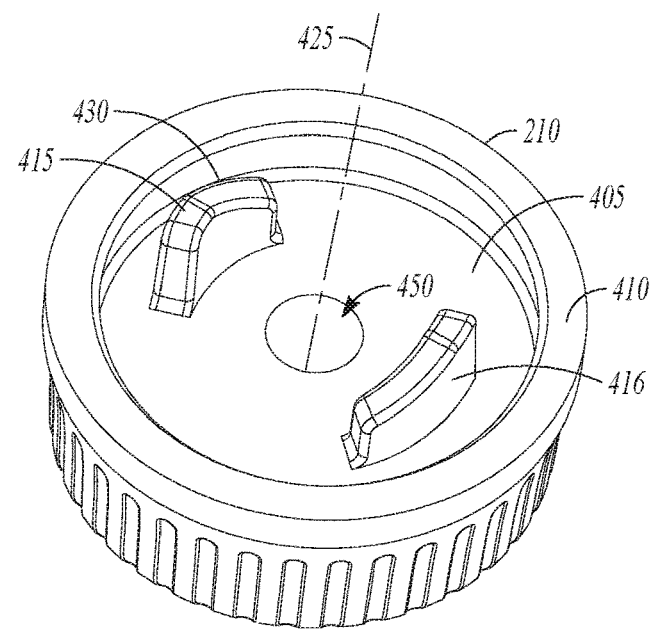
FIG. 4 is a perspective view of a bottom side of a manual input.
Figure 5:
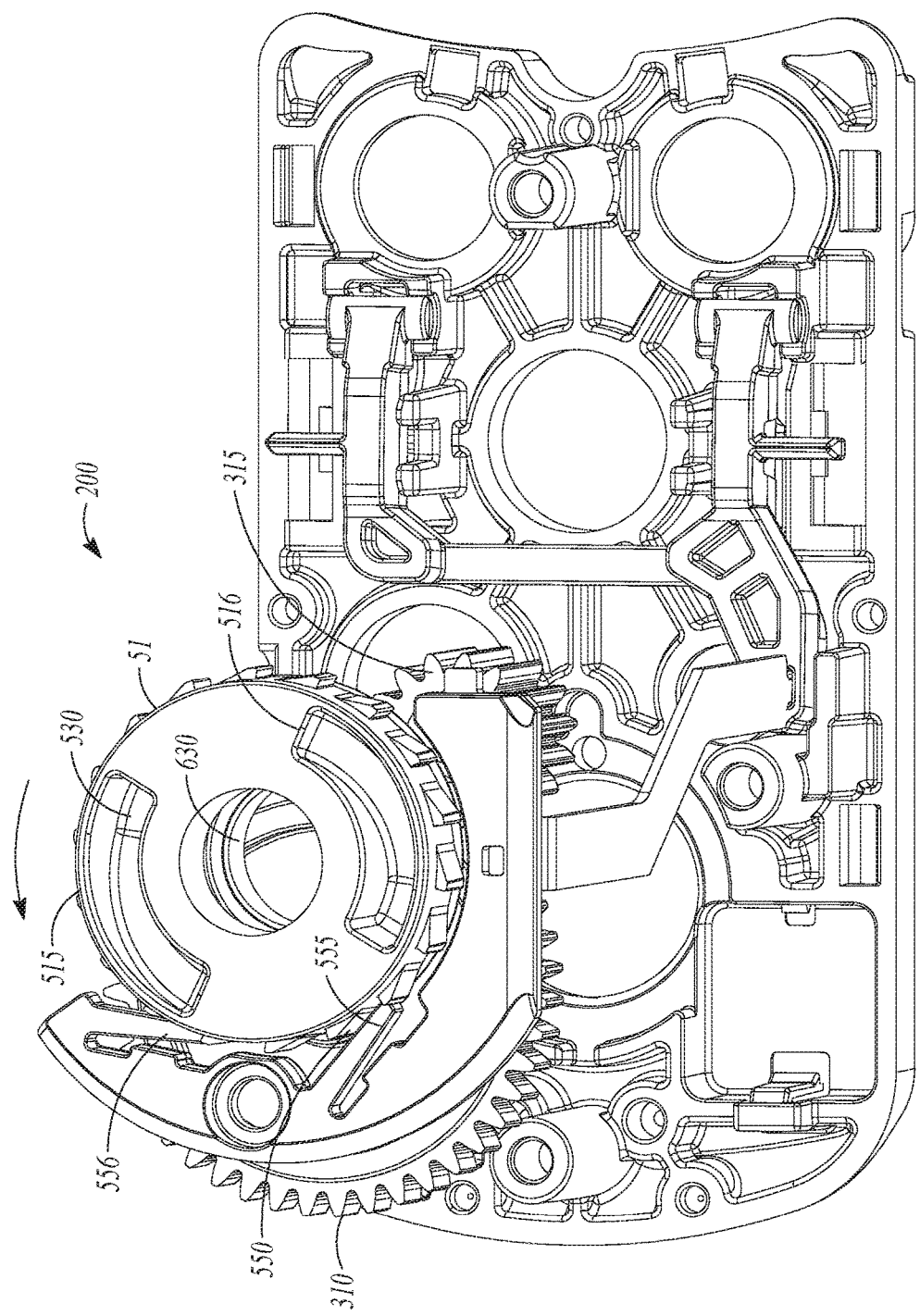
FIG. 5 is a top perspective view of components in the proximal end of the drive system, with the manual input removed.

FIG. 4 is a perspective view of a bottom side of the manual input 210. FIG. 5 is a top perspective view of components in the proximal end of the drive system, with the manual input removed. The manual input 210 (shown in FIG. 4) can be configured to engage with a coupling member 510 (shown in FIG. 5.) In an example, the coupling member can include a first engagement feature 515, which can for example include a recession in a top surface 525 of the coupling member, and the manual input 210 can include a second engagement feature 415, which can be a protrusion, that is sized and shaped to engage with the first engagement feature 515. The second engagement feature 415 can be located in a recession 405 in a bottom surface 410 of the manual input 210. While the first engagement feature 515 is shown as a recession and the second engagement feature 415 is shown as a protrusion, the parts can also be reversed, such that the manual input includes a protrusion and the coupling member 510 includes a recession, or both parts may include a protrusion.

The first engagement feature 515 can be shaped to extend around a circumferential path around a coupling member axis 520, and the second engagement feature 415 can be shaped to extend along a circumferential path around a manual input axis 425. The manual input 210 and coupling member 510 can be sized and shaped to align the manual input axis 420 with the coupling member axis 525. The alignment of the axes 425, 525 and the shaping of the engagement features can allow the manual input 210 to rotate with respect to the coupling member 510 around the aligned axes. In various examples, the first engagement feature 515 can include a ramp 530, the second engagement feature 415 can include a ramp 430, or both the first engagement feature 515 and the second engagement feature 415 can include a ramp. The presence of the ramp shape can cause the coupling member 510 to move distally with respect to the manual input 210 when the manual input is rotated in a first direction (indicated by arrow) with respect to the coupling member 510 in a rotational direction that presses the engagement features 415, 515 together. Turning the manual input 210 in a second direction may allow the coupling member to move proximally.

The manual input 210 and coupling member 510 can each optionally include more than one engagement feature. In the illustrated example, the manual input 210 includes a second manual input engagement feature 416, and the coupling member 510 includes second coupling member engagement feature 516. The manual input engagement feature 416 is shown as a protruding ramp, but could alternatively be a recession, i.e. the manual input 210 can include one protruding ramp and one recession, and the coupling member 510 can include one corresponding recession and one ramp that align with the features on the manual input 210. In other examples, the manual input 210 and coupling member 510 can each include three, four, or more engagement features that are sized and shaped to engage with each other and bias the coupling member 510 in the distal direction when the manual input is rotated.

Figure 6:
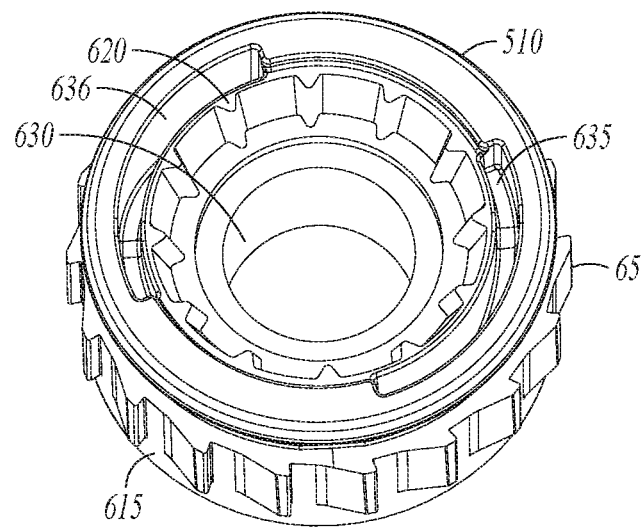
FIG. 6 is a perspective bottom view of a coupling component.

FIG. 6 is a perspective view of the bottom side 605 of the coupling member 510. The coupling member can include teeth 610 on an outer surface 615 that can be configured to engage with a ratchet 550 (shown in FIG. 5). The ratchet can include one or more ratchet arms 555, 556, that can engage with the coupling member teeth 610. The ratchet arms 555, 556, can provide a force that resists rotation of the coupling member 510 in the first direction (indicated by the arrow in FIG. 5). The ratchet arms 555, 556 can also be sized and shaped to prevent rotation of the coupling member 510 in a second direction opposition the first direction.

Figure 7:
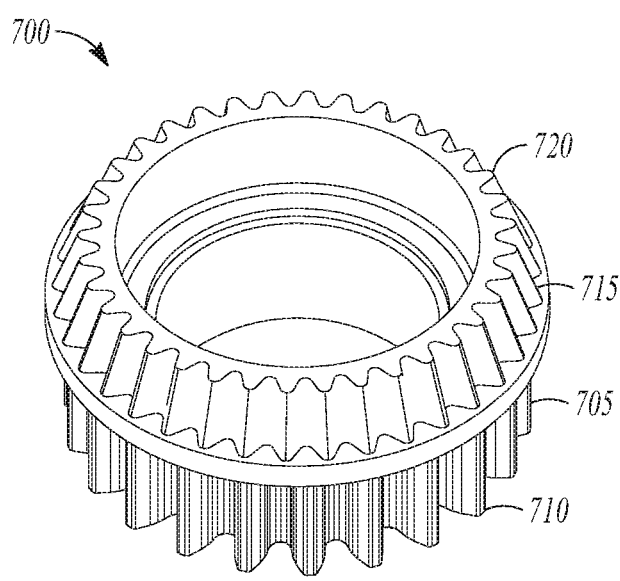
FIG. 7 is a perspective view of a first gear.

Referring again to FIG. 6, the coupling member 510 can include one or more engagement features 620 (shown in FIG. 6) that are sized and shaped to engage with the engagement features 720 on the first gear (shown in FIG. 7.) The coupling member 510 can also include a bore 630 that can receive a shaft.

FIG. 7 is a perspective view of first gear 700. The first gear can include a lower portion 705 that includes gear teeth 710 and an upper portion 715 that can include one or more engagement features 720. The engagement features 720 can be on a tapered portion 725 on a top (proximal) side 730 of the first gear 700. The engagement features 720 may, for example, be teeth. The tapered surface can be frustum-shaped (as shown), rounded, hemispherical, or otherwise configured to move in and out of engagement with the coupling member. While the first gear is depicted as a gear, in other types of drive systems, the first gear 700 can alternatively be configured differently. For example, in a belt-driven system, the first gear 700 can be a pulley and the gear teeth 710 can be a belt engagement surface.

Figure 8A:
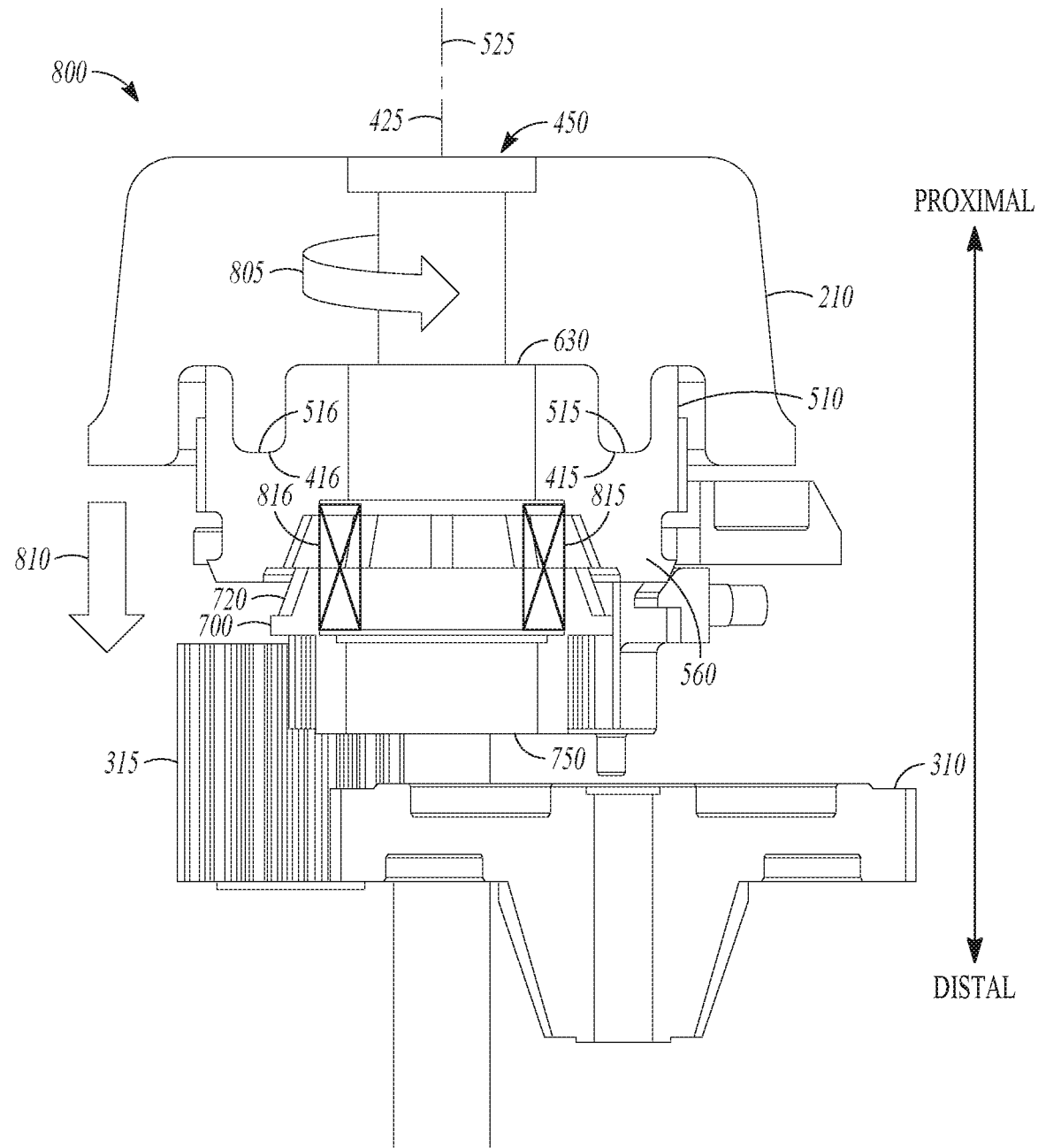
FIG. 8A is a cross-sectional view of drive components in the proximal end of the drive system, with the coupling member not engaged with the first gear.

FIG. 8A is a cross-sectional view of drive components 800 in the proximal end of the drive system 200, with the coupling member 510 not engaged with the first gear 700. The manual input 210 can be assembled onto the coupling member 510, which can be assembled above the first gear 700. The manual input can be rotated counter-clockwise (as indicated by the arrow 805), which rotates engagement features 415, 416 on the underside of the manual input 210 against engagement features 515, 516 on the top side of the coupling member, and biases the coupling member 510 in a distal direction (as indicated by the arrow 810). Moving the coupling member 510 distally can engage the coupling member 510 with the first gear 700. The coupling member can thus operate as an interlock, i.e. the coupling member can selectively couple and uncouple the manual input 210 with the first gear 700. In some examples, springs 815, 816 can be assembled between the manual coupling member 510 and the first gear 700 to bias the coupling member to an uncoupled position in which the coupling member 510 is not engaged with the spring. The manual input 210, coupling member 510, and first gear 700 can be assembled onto a shaft (not shown) that can extend through bores 450, 630, 750 in each of the assembled components and maintain axial alignment of the components.

Figure 8B:
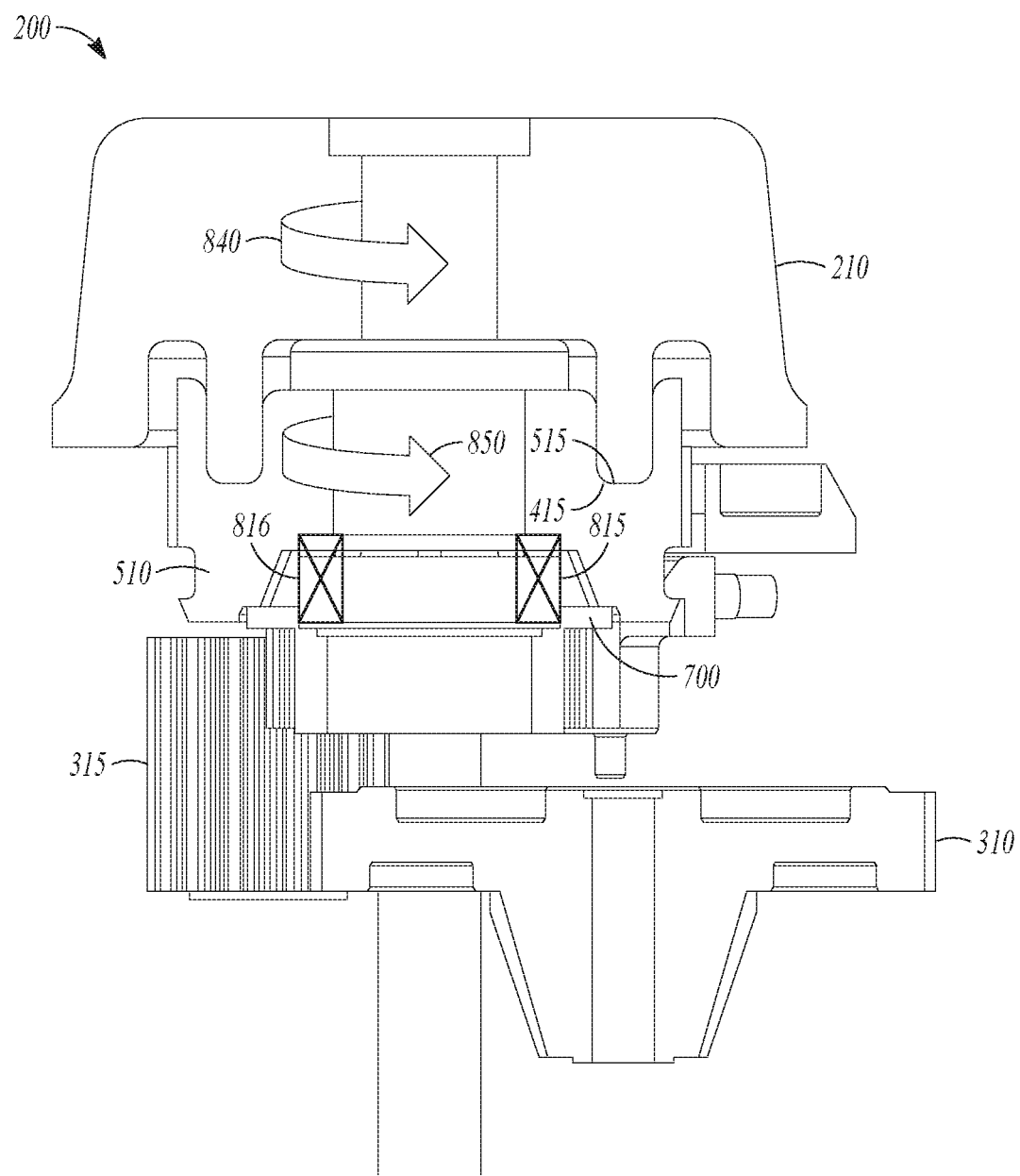
FIG. 8B is a cross-sectional view of drive components in the proximal end of the drive system, with the coupling member engaged with the first gear.

FIG. 8B is a cross-sectional view of drive components in the proximal end of the drive system 200, with the coupling member 510 engaged with the first gear 700. Rotation of the manual input 210 to advance the coupling member distally eventually produces the configuration shown in FIG. 8B, where the springs 815, 816 are compressed and the engagement features 620 on the distal side of the coupling member 510 are engaged with the engagement features 720 (e.g., tapered teeth) on the proximal side of the first gear 700. Rotation of the manual input 210 counter-clockwise (as indicated by arrow 840) rotates the coupling member 510, which rotates the first gear 700 (as indicated by arrow 850).

To retract a moveable element, a user can rotate the manual input 210 to advance the coupling member 510, compress the springs 815, 816 and engage the coupling member 510 with the gear 700 to engage a drive train that may retracts the moveable element, which may, for example, be a surgical instrument, or coupled to a surgical instrument.

Figure 8C:
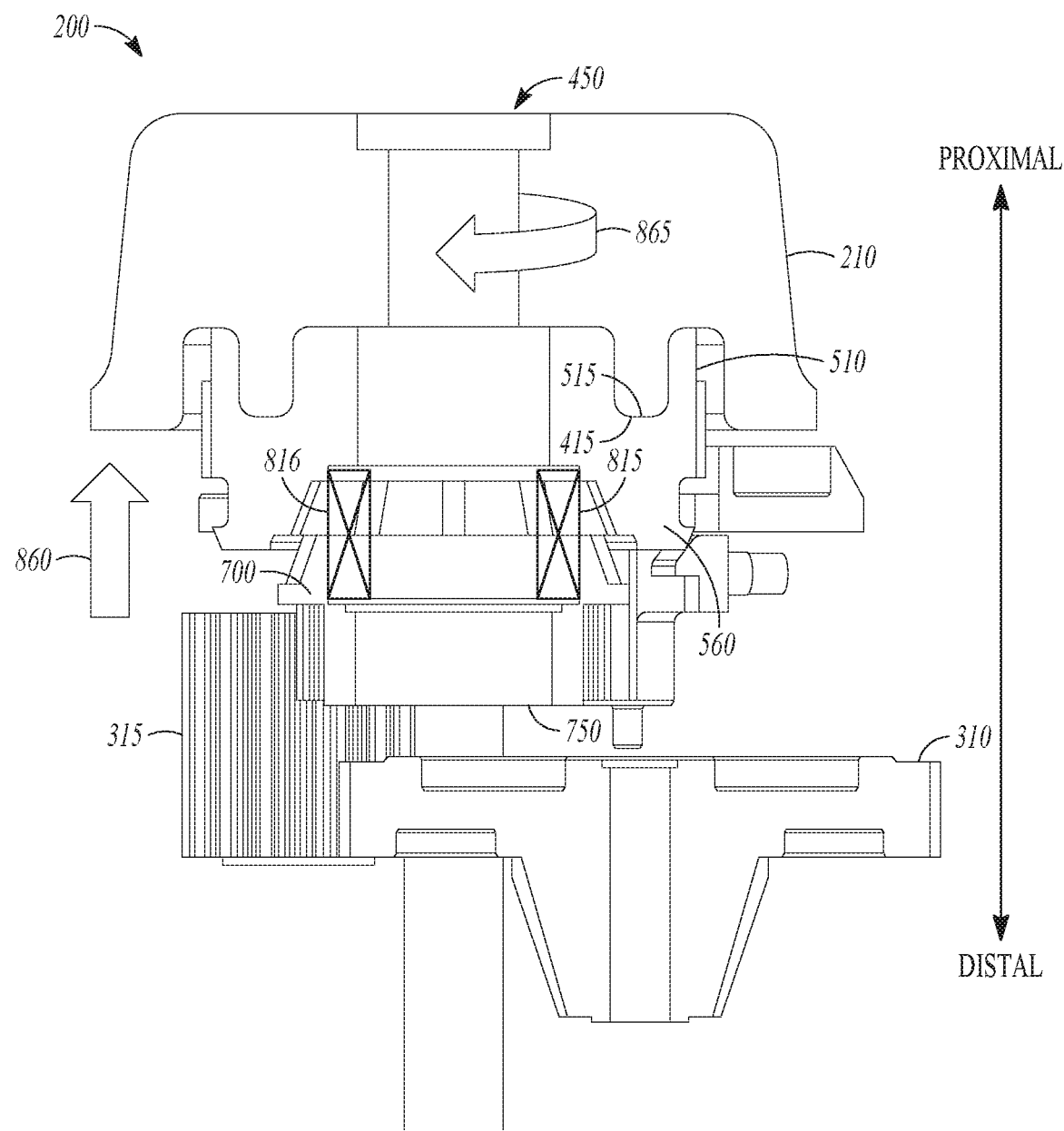
FIG. 8C is a cross-sectional view of drive components in the proximal end of the drive system, with springs biasing the coupling member away from the first gear.

FIG. 8C is a cross-sectional view of drive components in the proximal end of the drive system 200, with springs 815, 816 biasing the coupling member away from the first gear. When the manual input 210 is released, the springs 815, 816 exert an upward (proximal) force (indicated by arrow 860 on the coupling member 510, which drives the coupling member toward the manual input 210 and out of engagement with the first gear. In some examples, the springs also turn the manual input 210 in a clockwise direction (as indicated by arrow 865), for example as ramps on the coupling member 510 slide against ramps on the manual input 210. In FIG. 8C, the coupling member has slid to a most proximal position, and the coupling member 510 is disengaged from the first gear 700.

FIGS. 9 through 14B illustrate the operation of a manual drive lock 910 that may engage the coupling member 510. The manual drive lock 910 may include a locking element 920 that can move into and out of engagement with a locking feature 560 (such as a notch or groove) on the coupling member 510 that prevents the coupling member 560 from moving in a proximal direction when the manual input 210 is released.

Figure 9:
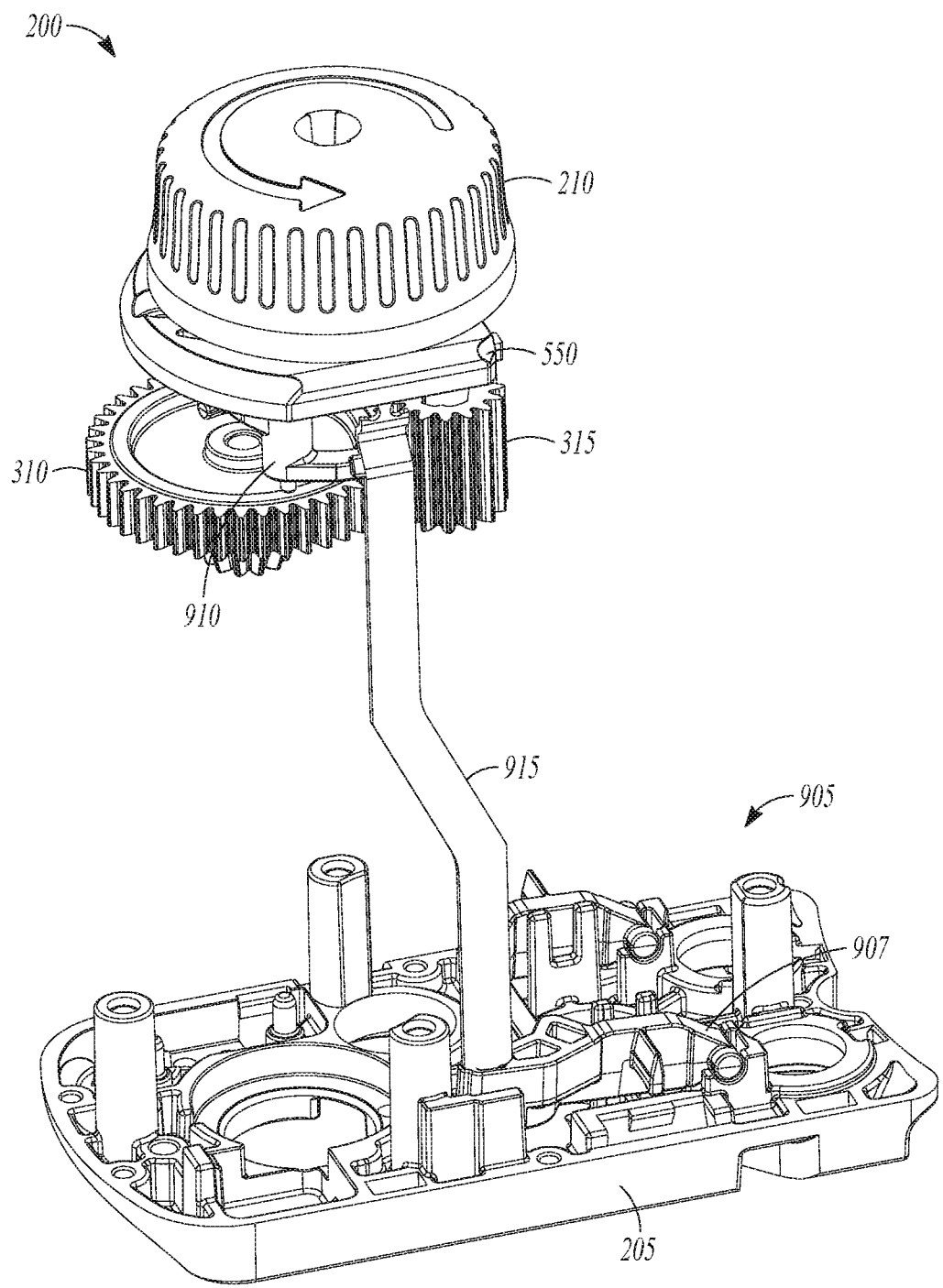
FIG. 9 is a perspective view of portions of the proximal end of the drive system that shows a lock switch and a lower chassis.

FIG. 9 is a perspective view of portions of the proximal end of the drive system that shows a lock switch 905 and a lower chassis 205. The lock switch 905 can be coupled to the manual drive lock 910. The lock switch 905 may, for example include a linkage 915 that couples a lower portion of the lock switch 907 with an upper portion of the lock switch (shown in FIG. 11). In another configuration, the lower portion 907 of the lock switch 905 may be directly connected to the upper portion 906 of the lock switch.

Figure 10:
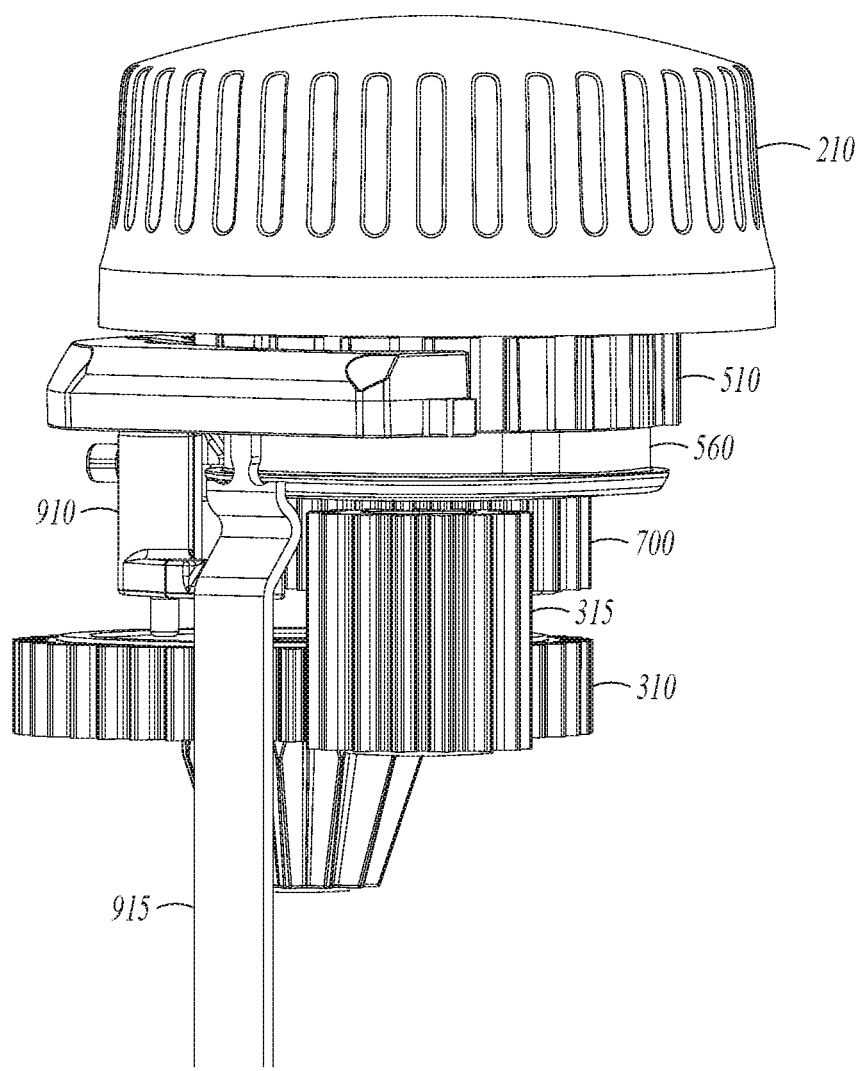
FIG. 10 is a side perspective view that shows drive components, the manual drive lock 910, and the locking feature on the coupling member.

FIG. 10 is a side perspective view that shows drive components, the manual drive lock 910, and the locking feature 560 on the coupling member 510.

Figure 11:
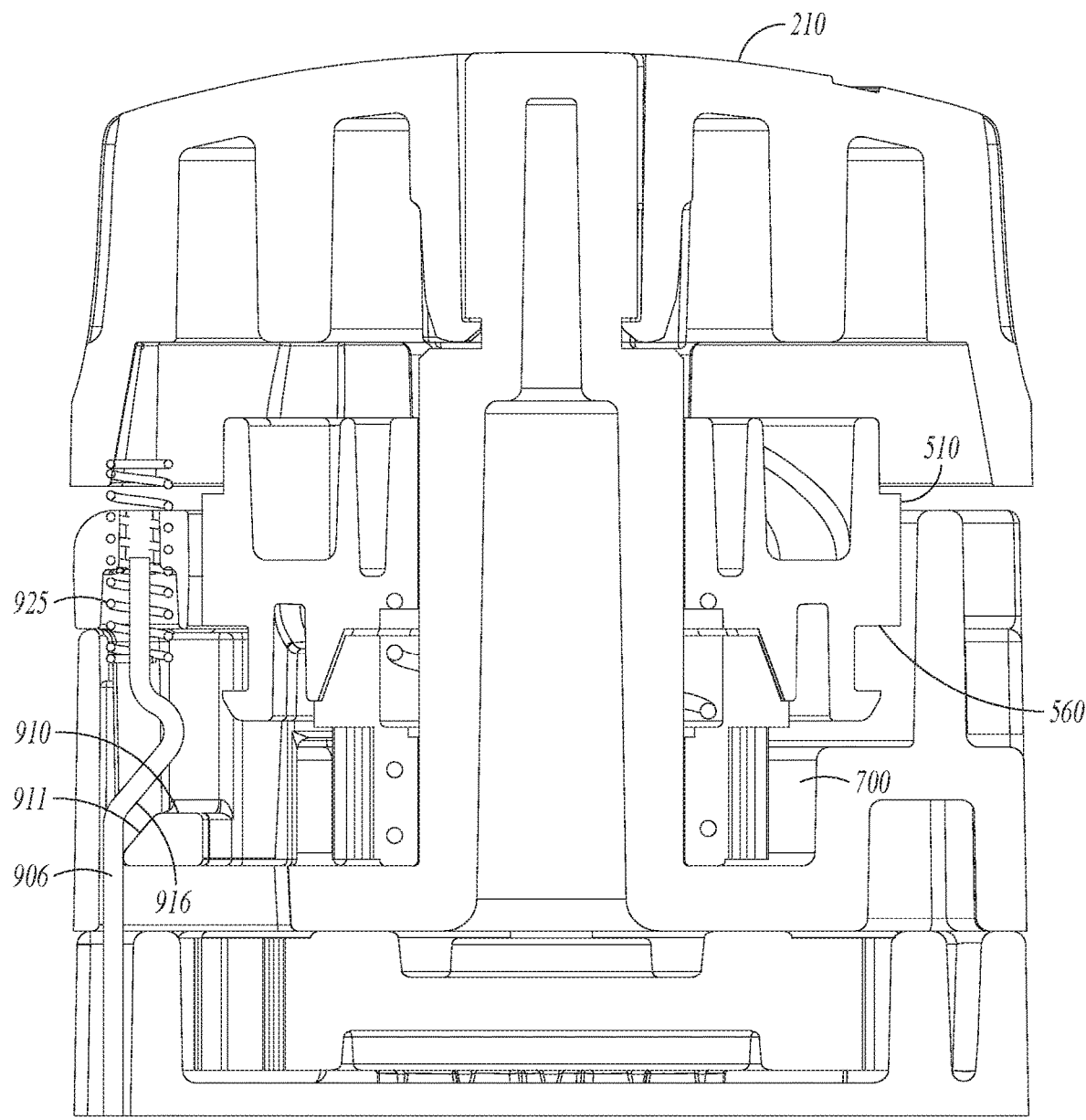
FIG. 11 is a cross-sectional view of drive components, an upper portion of the lock switch, and a portion of the manual drive lock engaged with the lock switch.

FIG. 11 is a cross-sectional view of drive components, an upper portion 906 of the lock switch 905, and a portion of the manual drive lock 910 engaged with the lock switch. The upper portion 906 of the lock switch 905 can include a ramp 916 that engages with a ramp 911 on the manual drive lock 910. The manual drive lock can be biased with a spring 1405 (shown in FIG. 14B) to rotate toward the locking feature 560 on the coupling member 510. The ramp 916 on the upper portion 906 of the lock switch prevents the manual drive lock 910 from rotating into engagement with the coupling member. A spring 925 can be coupled to the upper portion 906 of the lock switch 905 and configured to bias the lock switch down so that the ramp 916 on the lock switch remains in engagement with the ramp on the manual drive lock 910.

Figure 12A:
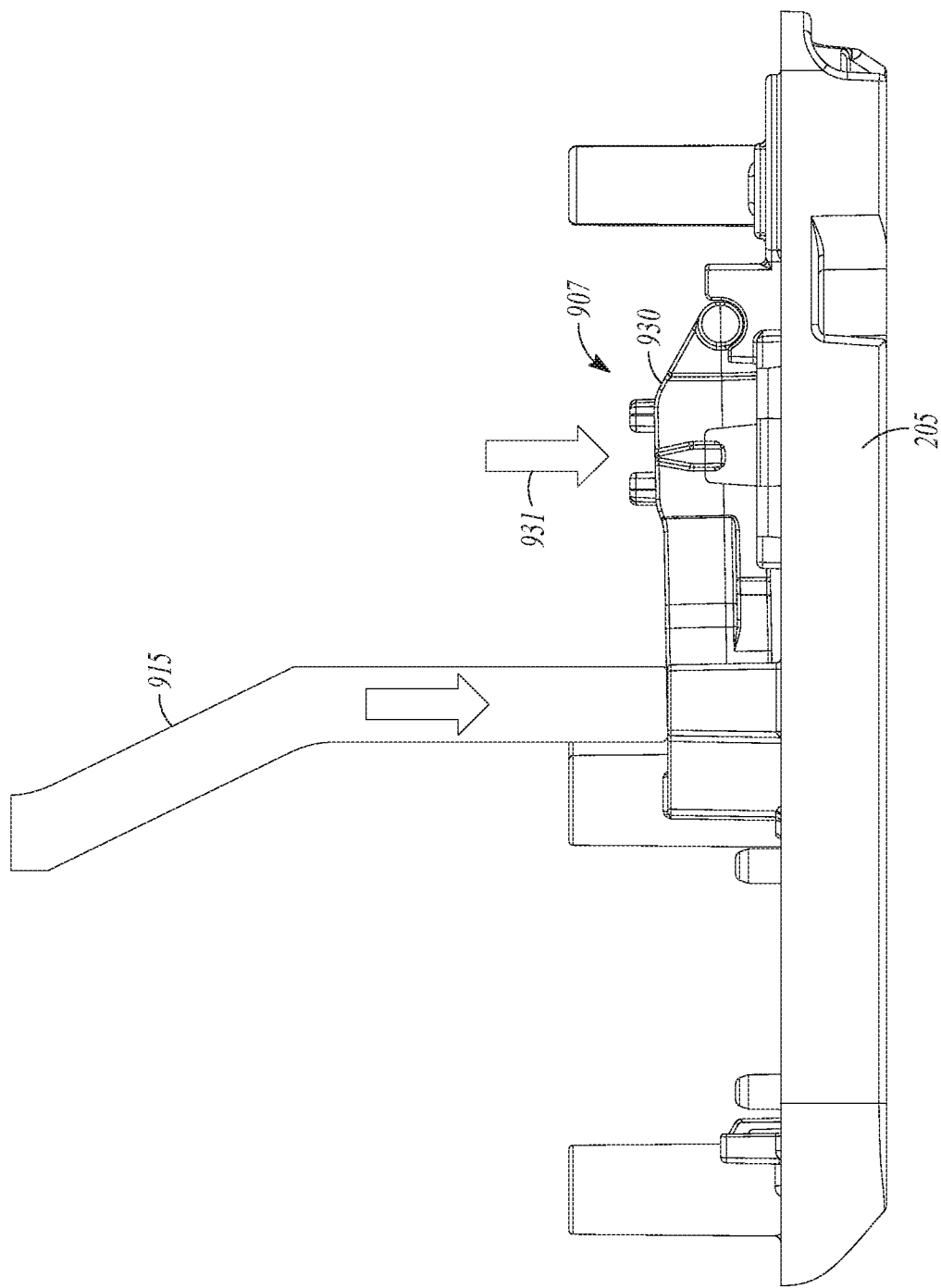
FIG. 12A is a side view of the lower portion of the lock switch, the lower chassis.
Figure 13A:
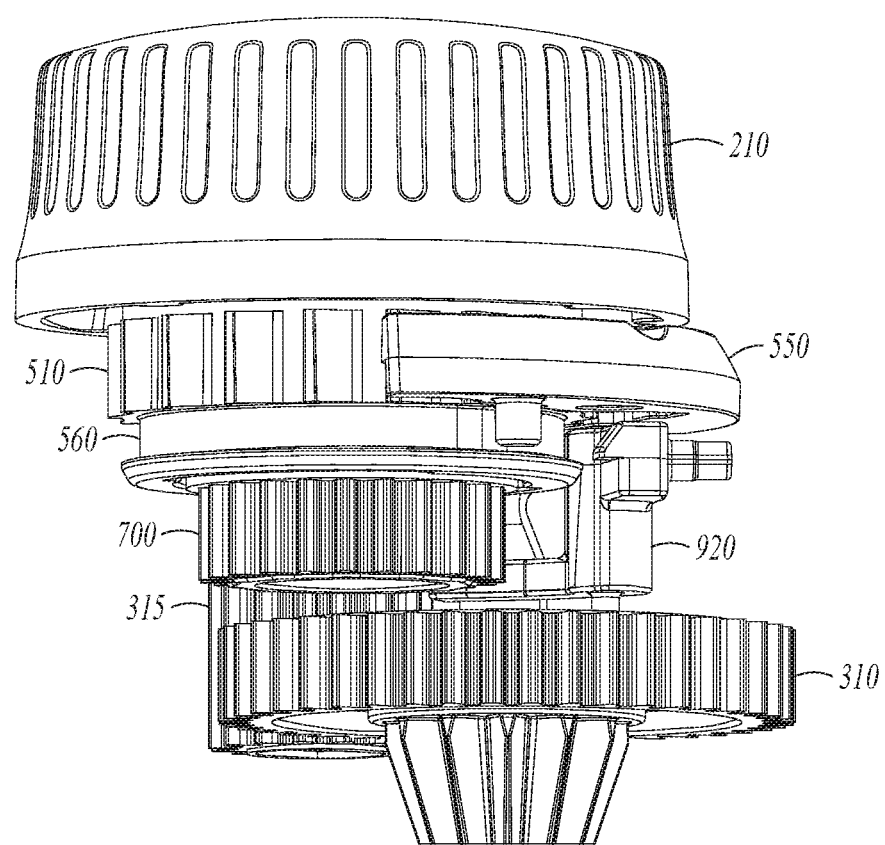
FIG. 13A is a perspective view showing the manual drive lock disengaged from the coupling member.
Figure 14A:
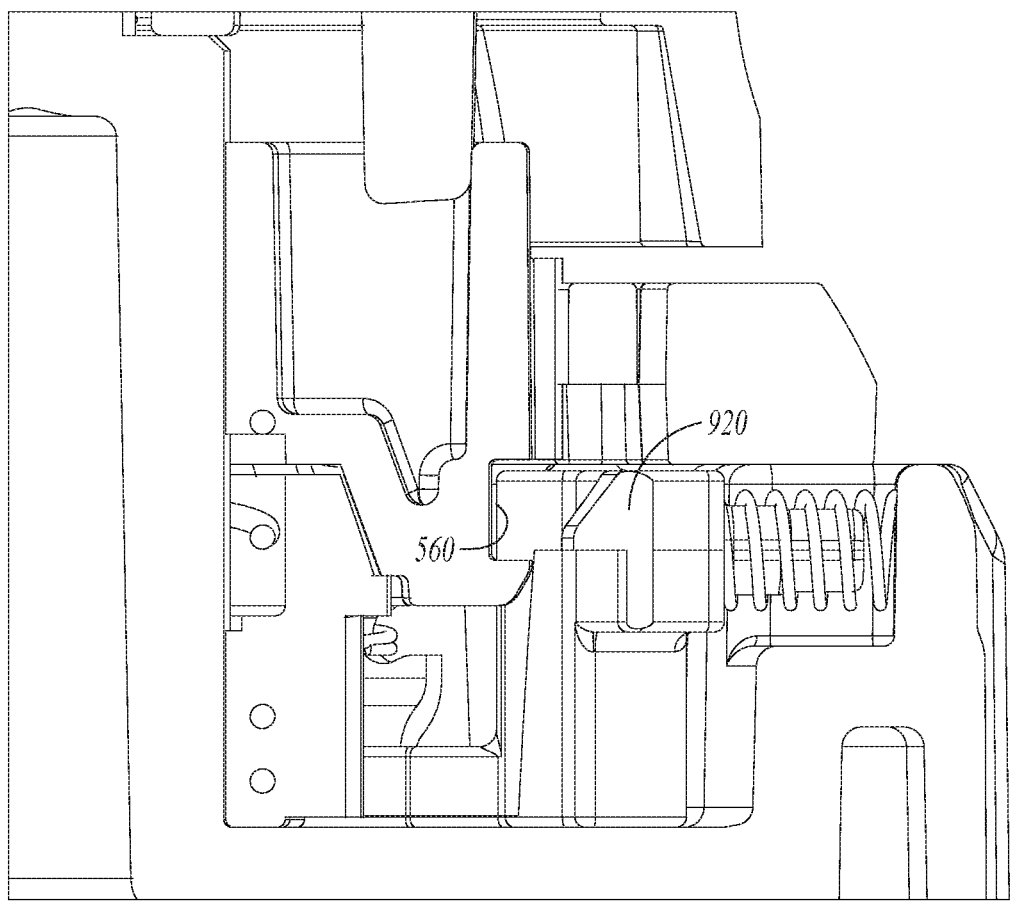
FIG. 14A is a perspective view showing the manual drive lock disengaged from the coupling member.

FIG. 12A is a side view of the lower portion 907 of the lock switch, the lower chassis 205. The lower portion 907 of the lock switch can include a lever 930. When the lever 930 is in a down position (as indicated by arrow 931), the upper portion 906 of the lock switch (shown in FIG. 11) retains the manual drive lock 910 in a disengaged position, as shown in FIG. 13A and FIG. 14A.

Figure 12B:
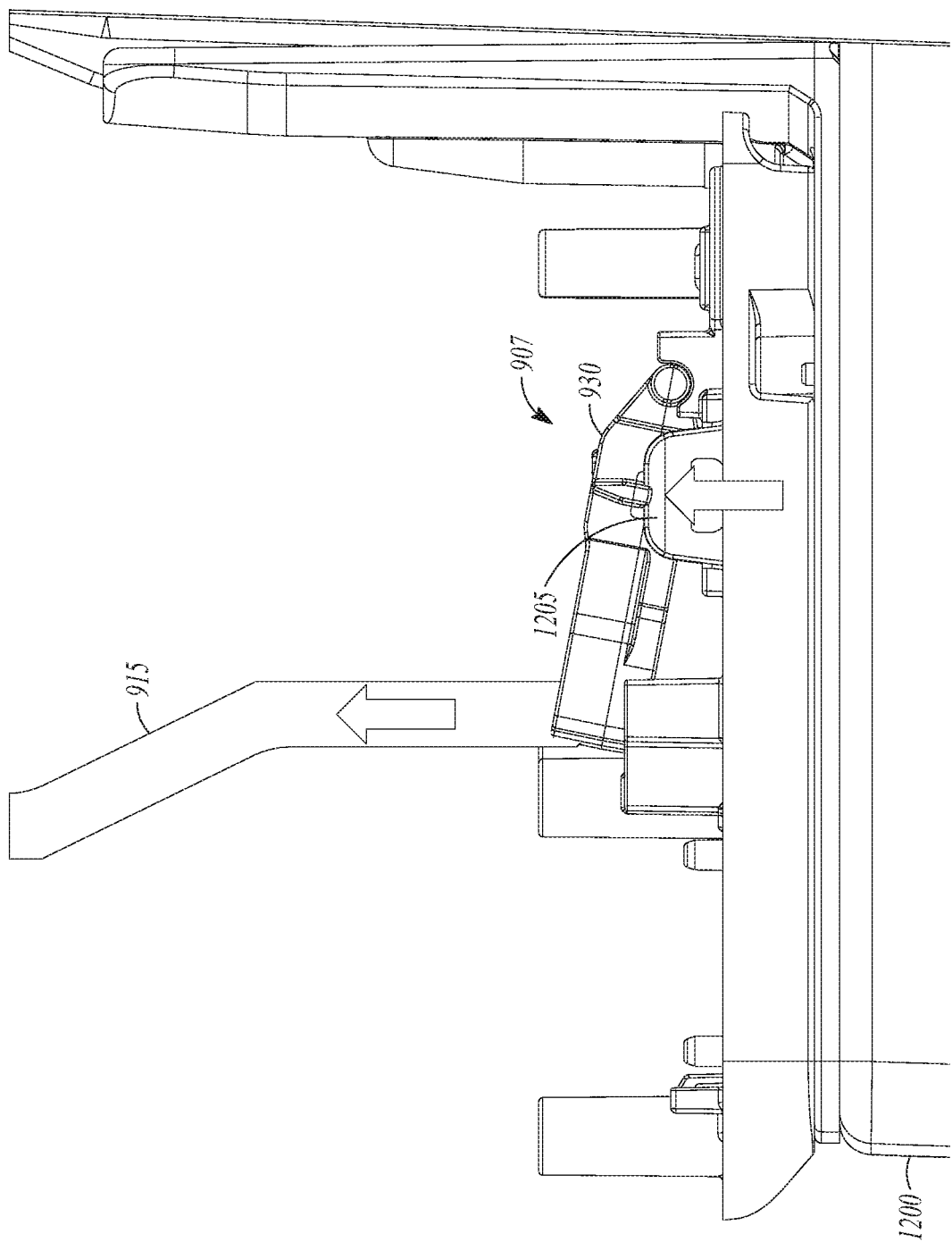
FIG. 12B is a side view of the lower portion of the lock switch, with an adapter coupled to the lower chassis.
Figure 13B:
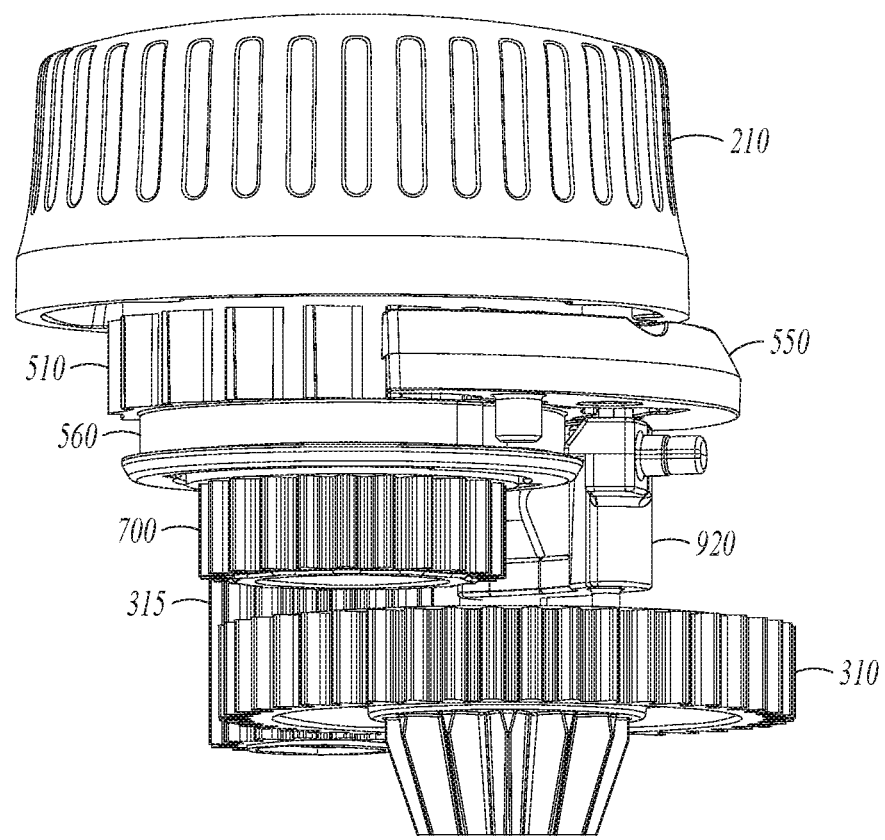
FIG. 13B is a perspective view showing the manual drive lock engaged with the coupling member.
Figure 14B:
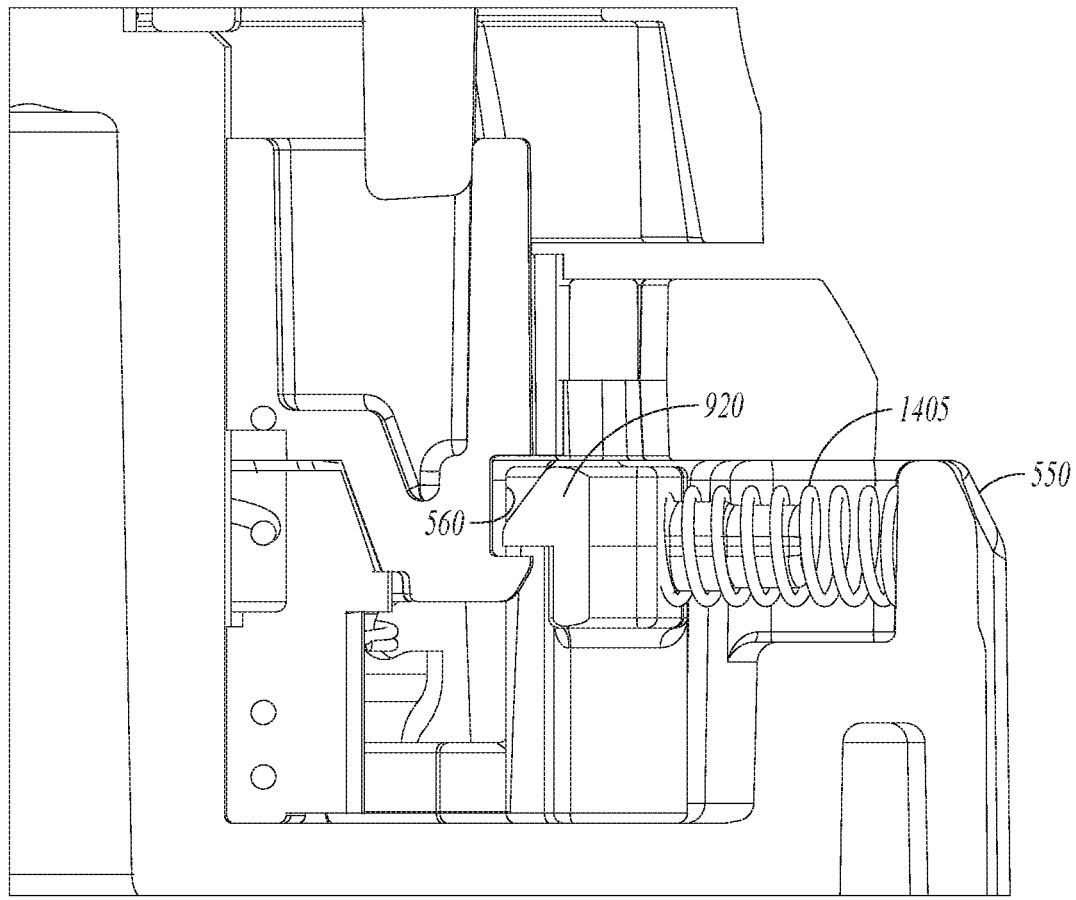
FIG. 14B is a perspective view showing the manual drive lock engaged with the coupling member.

FIG. 12B is a side view of the lower portion 907 of the lock switch, with an adapter 1200 coupled to the lower chassis 205. When the lever 930 is biased to an upward position (as indicated by arrow 1205), the lock switch 910 moves upward, and the upper portion 906 of the lock switch slides out of engagement with the manual drive lock 905, allowing the manual drive lock to rotate into engagement with the engagement feature (e.g. groove) 560 on the coupling member 510, as shown in FIG. 13B and FIG. 14B.

In an example, a latch 1210 on the adaptor 1200 may actuate the lever 930 to the upward position and thereby disengage the lock switch. With the lock switch 910 disengaged, the manual drive lock 905 may be free to rotate into engagement with the engagement feature 560 on the coupling member 510. In some example, the engagement feature 560 is sized and shaped so that the manual drive lock 905 can engage the coupling member only when the coupling member is in a lower (distal) position, in which the coupling member 510 is engaged with the first gear 700. In an example workflow, in a state in which the lock switch is biased upward, such as when the adaptor 1200 is coupled to the chassis 205 and the latch 1205 is engaged with the lever 930, when the manual input 210 is actuated to advance the coupling member 510 distally and engages the first gear 700, the manual drive lock rotates into engagement with the engagement feature (groove) 560 on the coupling member, which can lock the manual drive components in position and allow for manual retraction by rotation of the manual 210, without re-engaging the coupling member if the manual input is released.

Figure 15:
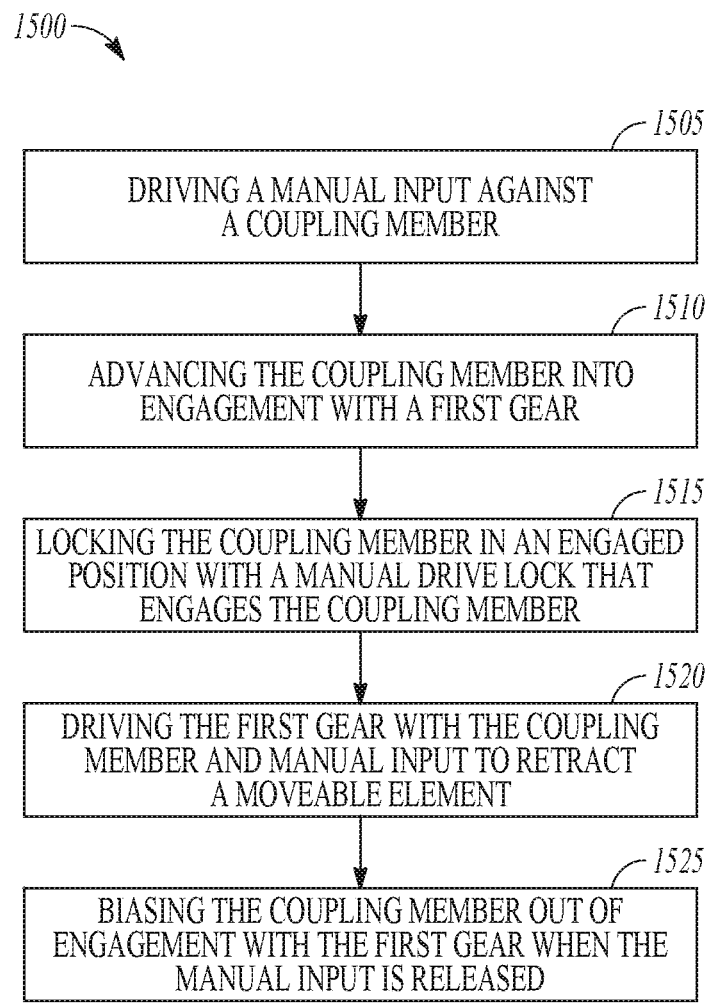
FIG. 15 is a flowchart illustrating an example method of controlling a surgical instrument.

FIG. 15 is a flowchart illustrating an example method 1500 of controlling a surgical instrument. At step 1505, a manual input such as manual input 210 is driven against a coupling member, such as coupling member 510. At step 1510, the coupling member is advanced into engagement with a first gear, such as gear 700. At step 1515, the coupling member is optionally locked into an engaged position, for example with a manual lock that engages the coupling member. At step 1520, the first gear is driven by the coupling member and the manual input by rotating the manual input, to retract a moveable element, which may for example be coupled to a surgical instrument inside a patient during a surgical procedure. The drive train may also optionally be driven by a computer-controlled system, with the manual drive input used for example during a power failure or system fault. At step 1525, the coupling member is biased out of engagement with the first gear when the manual input is released and the manual drive lock is in an unengaged position.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A surgical instrument, comprising:
    a surgical tool;
    a gear operably coupled to the surgical tool;
    a manual input member; and
    a coupling member positioned between the manual input member and the gear;

wherein on a condition that the coupling member is in a first position, the manual input member is operably coupled to drive rotation of the gear; and wherein on a condition that the coupling member is in a second position, the manual input member is operably decoupled from the gear.

2. The surgical instrument of claim 1, wherein:
the manual input member includes a protrusion positioned to engage the coupling member; and
the protrusion is positioned to transfer a rotational input from the manual input member to the coupling member.

3. The surgical instrument of claim 1, wherein:
the coupling member is slidably coupled to the manual input member; and
the coupling member moves longitudinally away from the manual input member as the manual input member is turned in a first direction.

4. The surgical instrument of claim 1, wherein:
the gear is a first gear;
the surgical instrument includes a second gear operably coupled between the coupling member and the first gear;
the coupling member includes a first set of gear teeth; and
the second gear includes a second set of gear teeth positioned to engage the first set of gear teeth of the coupling member.

5. The surgical instrument of claim 4, wherein:
a coaxial rotational axis is defined for the coupling member and the second gear;
the coupling member and the second gear are rotatable about the rotational axis;
the first set of gear teeth and the second set of gear teeth are arranged coaxially around the rotational axis; and
one of the first set of gear teeth or the second set of gear teeth is positioned radially outward of the other set of gear teeth.

6. The surgical instrument of claim 4, wherein:
a rotational axis is defined for the coupling member; and
the coupling member moves along the rotational axis relative to the first gear in response to a rotational input from the manual input member.

7. The surgical instrument of claim 4, wherein:
the surgical instrument includes a spring positioned between the coupling member and the second gear; and
the spring is positioned to bias the coupling member away from the second gear and to the second position.

8. The surgical instrument of claim 1, wherein:
the rotation is in a first direction;
the surgical instrument includes a rotational resistance member; and
the rotational resistance member resists a rotation of the coupling member in a second direction that is opposite the first direction.

9. The surgical instrument of claim 8, wherein:
a first moment is exerted on the coupling member by a rotation of the manual input member in the first direction;
a second moment is exerted on the coupling member by the rotation of the manual input member in the second direction; and
the first moment is greater than the second moment such that rotating the manual input member in the first direction rotates the coupling member.

10. The surgical instrument of claim 1, wherein:
one of the coupling member or the manual input member includes a ramp;

the other of the coupling member or the manual input member includes a protrusion positioned to engage the ramp; and
a rotation of the manual input member in a first direction engages the protrusion and the ramp and biases the coupling member away from the manual input member and toward the gear.

11. The surgical instrument of claim 1, wherein:
the surgical instrument includes a manual drive lock positioned to engage the coupling member; and
on conditions that the coupling member is in the first position, a torque is input to the manual input member to drive the coupling member, and the manual drive lock is actuated, the manual drive lock maintains the coupling member in the first position.

12. A surgical instrument, comprising:
a surgical tool;
a gear operably coupled to the surgical tool;
a manual input member; and
a coupling member positioned between the manual input member and the gear;
wherein the coupling member moves longitudinally between a first position and a second position in response to a rotation of the manual input member;
wherein the first position is distal to the second position;
wherein on a condition that the coupling member is in the first position, the manual input member is operably coupled to drive rotation of the gear; and
wherein on a condition that the coupling member is in the second position, the manual input member is operably decoupled from the gear.

13. The surgical instrument of claim 12, wherein:
the manual input member includes a protrusion positioned to engage the coupling member; and
the protrusion is positioned to transfer a rotational input from the manual input member to the coupling member.

14. The surgical instrument of claim 13, wherein:
the rotation is in a first direction;
the surgical instrument includes a rotational resistance member; and
the rotational resistance member resists a rotation of the coupling member in a second direction that is opposite the first direction.

15. The surgical instrument of claim 14, wherein:
a first moment is exerted on the coupling member by a rotation of the manual input member in the first direction;
a second moment is exerted on the coupling member by the rotation of the manual input member in the second direction; and
the first moment is greater than the second moment such that rotating the manual input member in the first direction rotates the coupling member.

16. The surgical instrument of claim 12, wherein:
the gear is a first gear;
the surgical instrument includes a second gear operably coupled between the coupling member and the first gear;
the coupling member includes a first set of gear teeth; and
the second gear includes a second set of gear teeth positioned to engage the first set of gear teeth of the coupling member.

17. The surgical instrument of claim 16, wherein:
a coaxial rotational axis is defined for the coupling member and the second gear;

the coupling member and the second gear are rotatable about the rotational axis;
the first set of gear teeth and the second set of gear teeth are arranged coaxially around the rotational axis; and
one of the first set of gear teeth or the second set of gear teeth is positioned radially outward of the other set of gear teeth.

18. The surgical instrument of claim 16, wherein:
on the condition that the coupling member is in the first position, the longitudinal movement of the coupling member places the first set of gear teeth in the second set of gear teeth in a meshed arrangement.

19. The surgical instrument of claim 16, wherein:
the surgical instrument includes a spring positioned between the coupling member and the second gear; and
the spring is positioned to bias the coupling member away from the second gear and to the second position.

20. The surgical instrument of claim 12, wherein:
one of the coupling member or the manual input member includes a ramp;
the other of the coupling member or the manual input member includes a protrusion positioned to engage the ramp; and
a rotation of the manual input member in a first direction engages the protrusion and the ramp to drive the longitudinal movement of the coupling member.

* * * * *